US010245182B2

(12) United States Patent
Scheller et al.

(10) Patent No.: US 10,245,182 B2
(45) Date of Patent: Apr. 2, 2019

(54) LASER PROBE WITH REPLACEABLE OPTIC FIBERS

(71) Applicant: Katalyst Surgical, LLC, Chesterfield, MO (US)

(72) Inventors: Gregg D Scheller, Wildwood, MO (US); Eric J Bass, Webster Groves, MO (US); Matthew N Yates, High Ridge, MO (US); Christina D McNiff, Troy, MO (US)

(73) Assignee: KATALYST SURGICAL, LLC, Chesterfield, MO (US)

(*) Notice: Subject to any disclaimer, the term of this patent is extended or adjusted under 35 U.S.C. 154(b) by 263 days.

(21) Appl. No.: 15/333,895

(22) Filed: Oct. 25, 2016

(65) Prior Publication Data

US 2017/0135859 A1 May 18, 2017

Related U.S. Application Data

(60) Provisional application No. 62/255,398, filed on Nov. 14, 2015.

(51) Int. Cl.
*G02B 6/36* (2006.01)
*G02B 6/38* (2006.01)
(Continued)

(52) U.S. Cl.
CPC .......... *A61F 9/00821* (2013.01); *A61B 18/22* (2013.01); *A61B 90/30* (2016.02);
(Continued)

(58) Field of Classification Search
CPC ...... A61F 9/00821; A61F 9/008; A61B 90/30; A61B 18/22; G02B 6/36; G02B 6/3806
(Continued)

(56) References Cited

U.S. PATENT DOCUMENTS 3,174,851 A 3/1965 Buehler et al.
4,122,853 A 10/1978 Smith
(Continued)

FOREIGN PATENT DOCUMENTS

EP 0900547 B1 3/1999
WO WO 2011/019581 A1 2/2001
(Continued)

OTHER PUBLICATIONS

H. Fischer, B. Vogel, W. Pfleging, H. Besser, Flexible distal tip made of nitinol (NiTi) for a steerable endoscopic camera system, Materials Science and Engineering A273-275 (1999) 780-783.
(Continued)

*Primary Examiner* — Gary Jackson
*Assistant Examiner* — Sebastian X Lukjan

(57) ABSTRACT

A laser probe with replaceable optic fibers may include a handle, an optic fiber fixture, and a replaceable optic fiber. The replaceable optic fiber may include an optic fiber having an optic fiber distal end and an optic fiber proximal end. The optic fiber may be disposed in a first transitory connector having a first transitory connector distal end and a first transitory connector proximal end wherein the optic fiber distal end extends a fixed distance from the transitory connector distal end. The optic fiber may be disposed in a second transitory connector having a second transitory connector distal end and a second transitory connector proximal end wherein the optic fiber proximal end extends a fixed distance from the second transitory connector distal end. The first transitory connector may be inserted in the handle and the second transitory connector may be inserted in the optic fiber fixture.

16 Claims, 23 Drawing Sheets

(51) Int. Cl.
  *A61B 17/00* (2006.01)
  *A61B 18/00* (2006.01)
  *A61B 18/22* (2006.01)
  *A61B 90/00* (2016.01)
  *A61B 90/30* (2016.01)
  *A61F 9/008* (2006.01)

(52) U.S. Cl.
  CPC ............... *A61F 9/008* (2013.01); *G02B 6/36* (2013.01); *G02B 6/3806* (2013.01); *A61B 17/00234* (2013.01); *A61B 2017/003* (2013.01); *A61B 2017/00477* (2013.01); *A61B 2018/00404* (2013.01); *A61B 2018/00589* (2013.01); *A61B 2090/0813* (2016.02); *A61B 2090/0814* (2016.02); *A61B 2090/306* (2016.02); *A61F 2009/00863* (2013.01)

(58) Field of Classification Search
  USPC .......................................................... 606/4
  See application file for complete search history.

(56) References Cited

U.S. PATENT DOCUMENTS

| | | |
|---|---|---|
| 4,147,443 A | 4/1979 | Skobel |
| 4,687,293 A | 8/1987 | Randazzo |
| 4,744,360 A | 5/1988 | Bath |
| 4,870,952 A * | 10/1989 | Martinez ............ A61B 1/00117 362/572 |
| 5,190,050 A | 3/1993 | Nitzsche |
| 5,228,852 A | 7/1993 | Goldsmith et al. |
| 5,257,988 A | 11/1993 | L'Esperance, Jr. |
| 5,322,055 A | 6/1994 | Davison et al. |
| 5,322,064 A | 6/1994 | Lundquist |
| 5,355,871 A | 10/1994 | Hurley et al. |
| 5,381,782 A | 1/1995 | DeLaRama et al. |
| 5,439,000 A | 8/1995 | Gunderson et al. |
| 5,454,794 A | 10/1995 | Narciso et al. |
| 5,520,222 A | 5/1996 | Chikama |
| 5,735,842 A | 4/1998 | Kruege et al. |
| 5,855,577 A | 1/1999 | Murphy-Chutorian et al. |
| 5,873,865 A | 2/1999 | Horzewski et al. |
| 5,951,544 A | 9/1999 | Konwitz |
| 6,123,699 A | 9/2000 | Webster, Jr. |
| 6,126,654 A | 10/2000 | Giba et al. |
| 6,178,354 B1 | 1/2001 | Gibson |
| 6,198,974 B1 | 3/2001 | Webster, Jr. |
| 6,330,837 B1 | 12/2001 | Charles et al. |
| 6,352,531 B1 | 3/2002 | O'Connor et al. |
| 6,488,695 B1 | 12/2002 | Hickingbotham |
| 6,505,530 B2 | 1/2003 | Adler et al. |
| 6,530,913 B1 | 3/2003 | Giba et al. |
| 6,533,772 B1 | 3/2003 | Sherts et al. |
| 6,551,302 B1 | 4/2003 | Rosinko et al. |
| 6,554,794 B1 | 4/2003 | Mueller et al. |
| 6,572,608 B1 | 6/2003 | Lee et al. |
| 6,620,153 B2 | 9/2003 | Mueller et al. |
| 6,730,076 B2 | 5/2004 | Hickingbotham |
| 6,863,668 B2 | 3/2005 | Gillespie et al. |
| 6,872,214 B2 | 3/2005 | Sonnenschein et al. |
| 6,984,230 B2 | 1/2006 | Scheller et al. |
| 7,004,957 B1 | 2/2006 | Dampney et al. |
| 7,226,444 B1 | 6/2007 | Ellman et al. |
| 7,303,533 B2 | 12/2007 | Johansen et al. |
| 7,402,158 B2 | 7/2008 | Scheller et al. |
| 7,555,327 B2 | 6/2009 | Matlock |
| 7,632,242 B2 | 12/2009 | Griffin et al. |
| 7,766,904 B2 | 10/2010 | McGowan, Sr. et al. |
| 7,935,108 B2 | 5/2011 | Baxter et al. |
| 8,038,692 B2 | 10/2011 | Valencia et al. |
| 8,075,553 B2 | 12/2011 | Scheller et al. |
| 8,197,468 B2 | 6/2012 | Scheller et al. |
| 8,840,605 B2 | 9/2014 | Scheller et al. |
| 8,840,607 B2 | 9/2014 | Scheller et al. |
| 8,968,277 B2 | 1/2015 | Scheller et al. |
| 8,951,245 B2 | 2/2015 | Scheller et al. |
| 9,023,019 B2 | 5/2015 | Scheller et al. |
| 9,023,020 B2 | 5/2015 | Scheller et al. |
| 9,039,686 B2 | 5/2015 | Scheller et al. |
| 9,089,399 B2 | 7/2015 | Scheller et al. |
| 9,107,682 B2 | 8/2015 | Scheller et al. |
| 9,113,995 B2 | 8/2015 | Scheller et al. |
| 9,119,702 B2 | 9/2015 | Scheller et al. |
| 2003/0171762 A1 | 9/2003 | Forchette et al. |
| 2004/0181138 A1 | 9/2004 | Hindricks et al. |
| 2004/0249367 A1 | 12/2004 | Saadat et al. |
| 2005/0054900 A1 | 3/2005 | Mawn et al. |
| 2005/0131399 A1 | 6/2005 | Loeb et al. |
| 2005/0154379 A1 | 7/2005 | McGowen, Sr. et al. |
| 2005/0157985 A1 | 7/2005 | McGowan, Sr. et al. |
| 2005/0234437 A1 | 10/2005 | Baxter et al. |
| 2005/0272975 A1 * | 12/2005 | McWeeney ........ A61B 1/00071 600/113 |
| 2005/0277874 A1 | 12/2005 | Selkee |
| 2006/0129175 A1 | 6/2006 | Griffen et al. |
| 2006/0178674 A1 | 8/2006 | McIntyre |
| 2006/0293270 A1 | 12/2006 | Adamis et al. |
| 2007/0179475 A1 | 8/2007 | Scheller |
| 2007/0185514 A1 | 8/2007 | Kirchhevel |
| 2007/0260231 A1 * | 11/2007 | Rose ...................... A61B 18/22 606/13 |
| 2008/0132761 A1 | 6/2008 | Sonnenschein et al. |
| 2008/0208105 A1 | 8/2008 | Zelickson et al. |
| 2008/0287938 A1 | 11/2008 | Scheller et al. |
| 2009/0018993 A1 | 1/2009 | Dick et al. |
| 2009/0163943 A1 | 6/2009 | Cavanaugh et al. |
| 2009/0187170 A1 | 7/2009 | Auld et al. |
| 2009/0312750 A1 | 12/2009 | Spaide |
| 2010/0004642 A1 | 1/2010 | Lumpkin |
| 2010/0191224 A1 | 7/2010 | Butcher |
| 2010/0268234 A1 | 10/2010 | Aho et al. |
| 2010/0331883 A1 | 12/2010 | Schmitz et al. |
| 2011/0028947 A1 | 2/2011 | Scheller et al. |
| 2011/0144627 A1 | 6/2011 | Smith |
| 2011/0144630 A1 | 6/2011 | Loeb |
| 2011/0280653 A1 | 11/2011 | Sjostedt et al. |
| 2012/0116361 A1 | 5/2012 | Hanlon et al. |
| 2012/0121222 A1 * | 5/2012 | Castonguay ......... G02B 6/3846 385/78 |
| 2012/0245569 A1 | 9/2012 | Papac et al. |
| 2013/0035551 A1 | 2/2013 | Yu et al. |
| 2013/0060240 A1 | 3/2013 | Scheller et al. |
| 2013/0071507 A1 | 3/2013 | Scheller et al. |
| 2013/0090635 A1 | 4/2013 | Mansour |
| 2013/0096541 A1 | 4/2013 | Scheller et al. |
| 2013/0116671 A1 | 5/2013 | Scheller et al. |
| 2013/0144278 A1 | 6/2013 | Papac et al. |
| 2013/0150838 A1 | 6/2013 | Scheller et al. |
| 2013/0165910 A1 | 6/2013 | Scheller et al. |
| 2013/0261610 A1 | 10/2013 | LaConte et al. |
| 2013/0281994 A1 | 10/2013 | Scheller et al. |
| 2013/0304043 A1 | 11/2013 | Scheller et al. |
| 2013/0304048 A1 | 11/2013 | Scheller et al. |
| 2013/0329446 A1 * | 12/2013 | Mansour ............... G02B 6/0005 362/553 |
| 2014/0005642 A1 | 1/2014 | Scheller et al. |
| 2014/0039471 A1 | 2/2014 | Scheller et al. |
| 2014/0039472 A1 | 2/2014 | Scheller et al. |
| 2014/0039475 A1 | 2/2014 | Scheller et al. |
| 2014/0046307 A1 | 2/2014 | Scheller et al. |
| 2014/0052115 A1 | 2/2014 | Zeid et al. |
| 2014/0066907 A1 | 3/2014 | Scheller et al. |
| 2014/0066912 A1 | 3/2014 | Scheller et al. |
| 2014/0074073 A1 | 3/2014 | Scheller et al. |
| 2014/0074079 A1 | 3/2014 | Scheller et al. |
| 2014/0088572 A1 | 3/2014 | Scheller et al. |
| 2014/0088576 A1 | 3/2014 | Scheller et al. |
| 2014/0107628 A1 | 4/2014 | Scheller et al. |

(56) References Cited

U.S. PATENT DOCUMENTS

2014/0107629 A1    4/2014   Scheller et al.
2015/0038950 A1    2/2015   Scheller et al.

FOREIGN PATENT DOCUMENTS

WO    WO 2006/091597 A1    8/2006
WO    WO 2007/038433 A2    4/2007
WO    WO 2013/133717        9/2013

OTHER PUBLICATIONS

Ferry P.W. Melchels, Jan Feijen, Dirk W. Grijpma, A review on stereolithography and its applications in biomedical engineering, Biomaterials 31 (2010) 6121-6130.

* cited by examiner

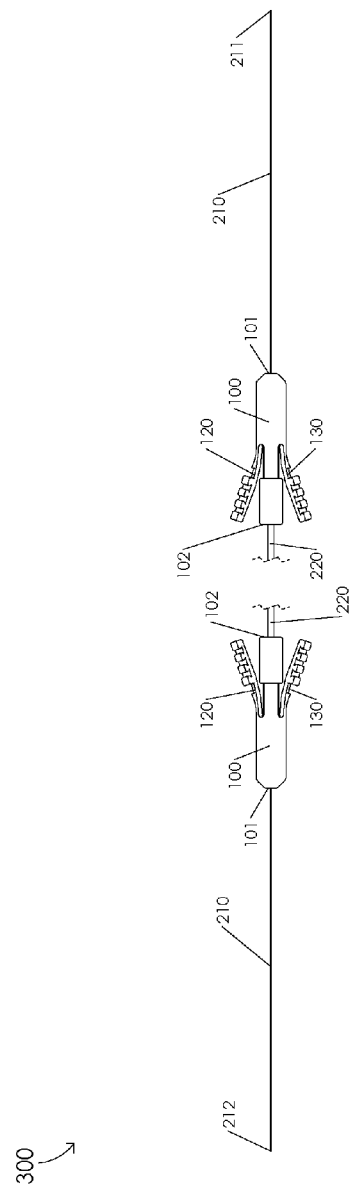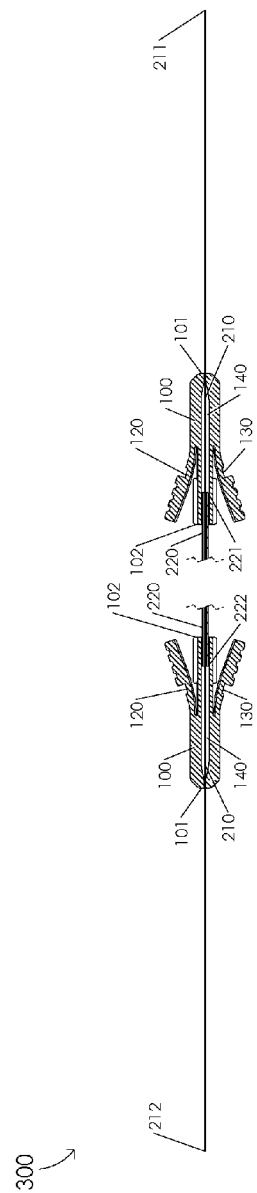

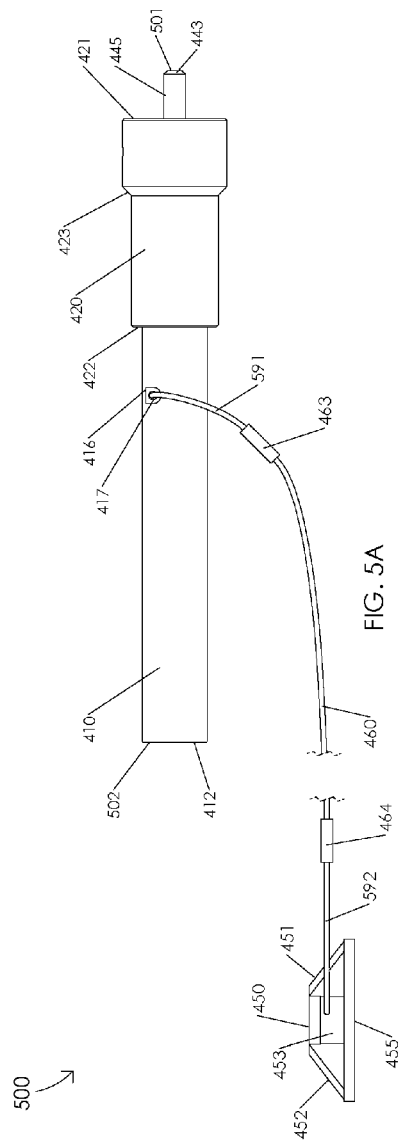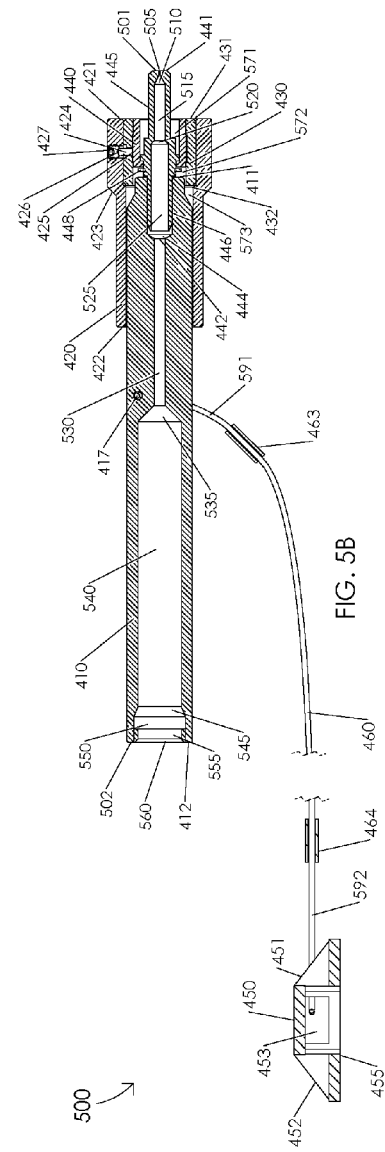

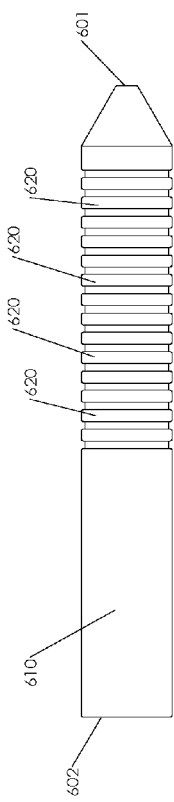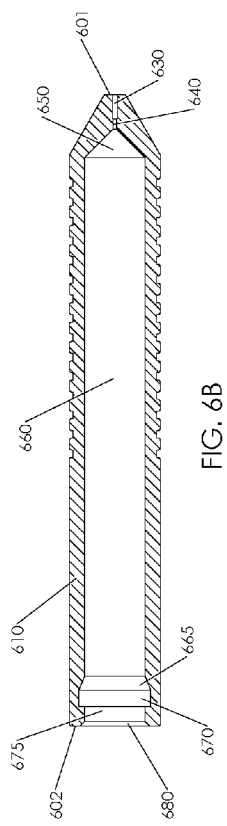
FIG. 6A
FIG. 6B

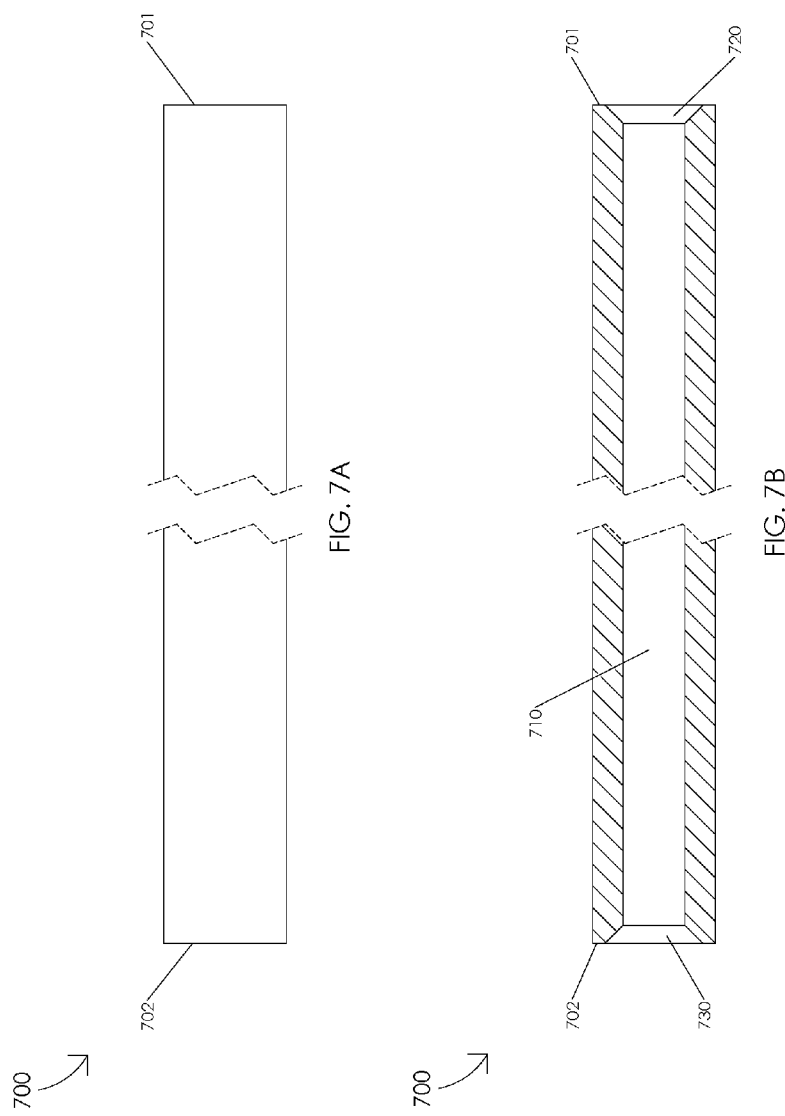

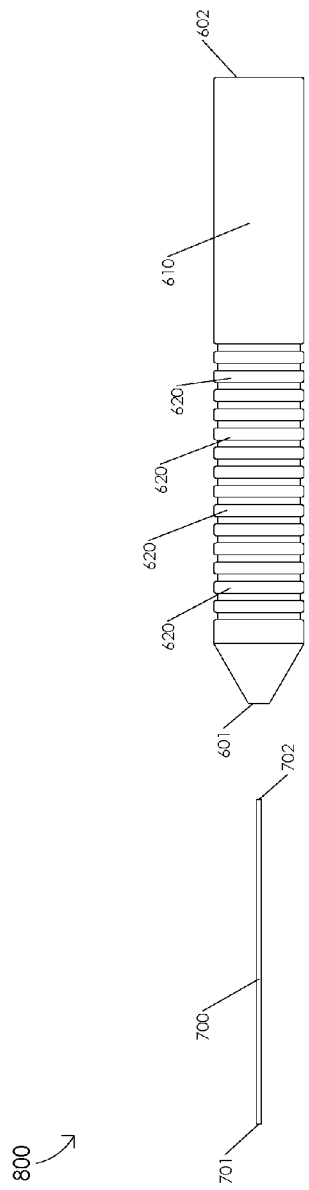
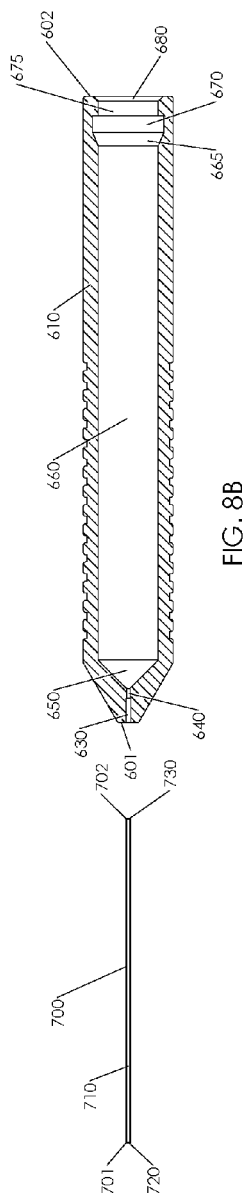

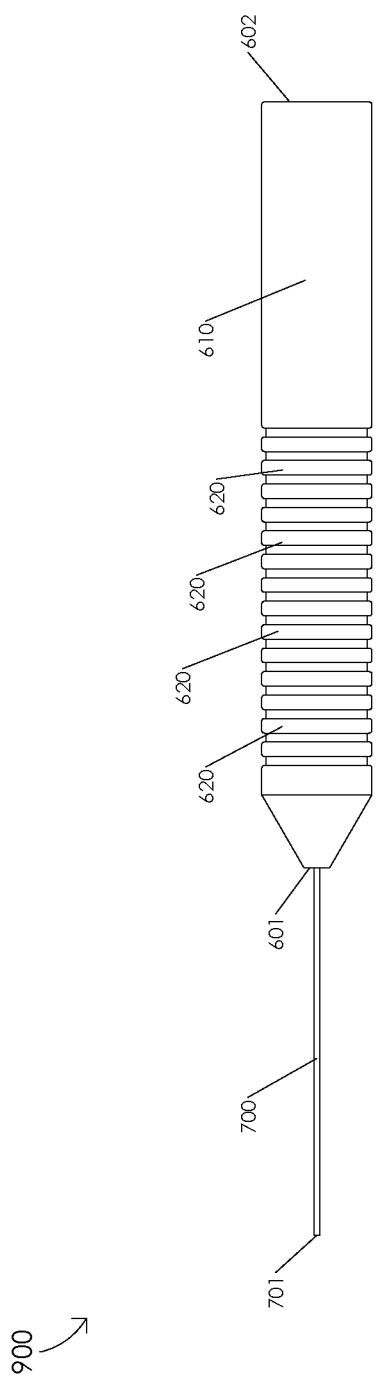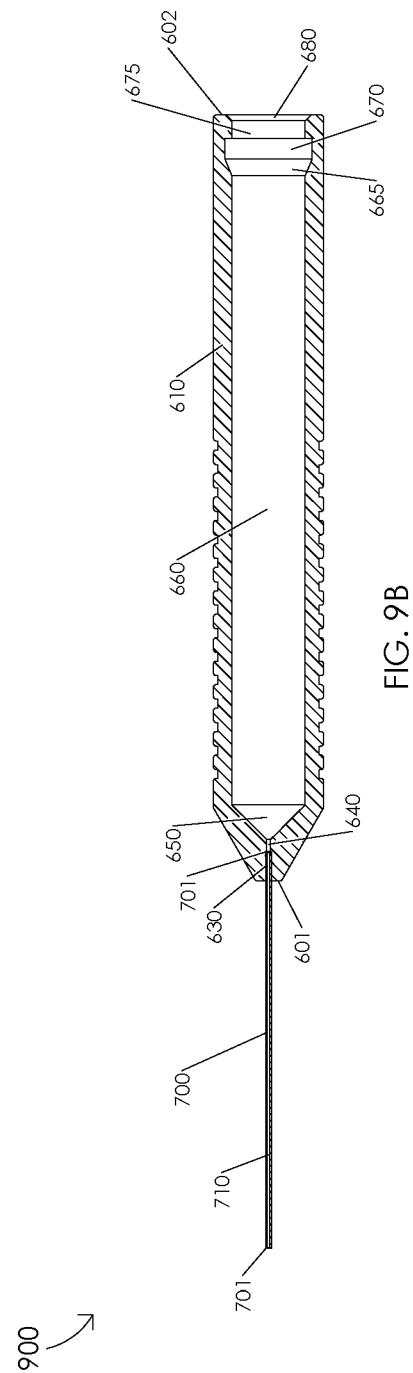
FIG. 9A
FIG. 9B

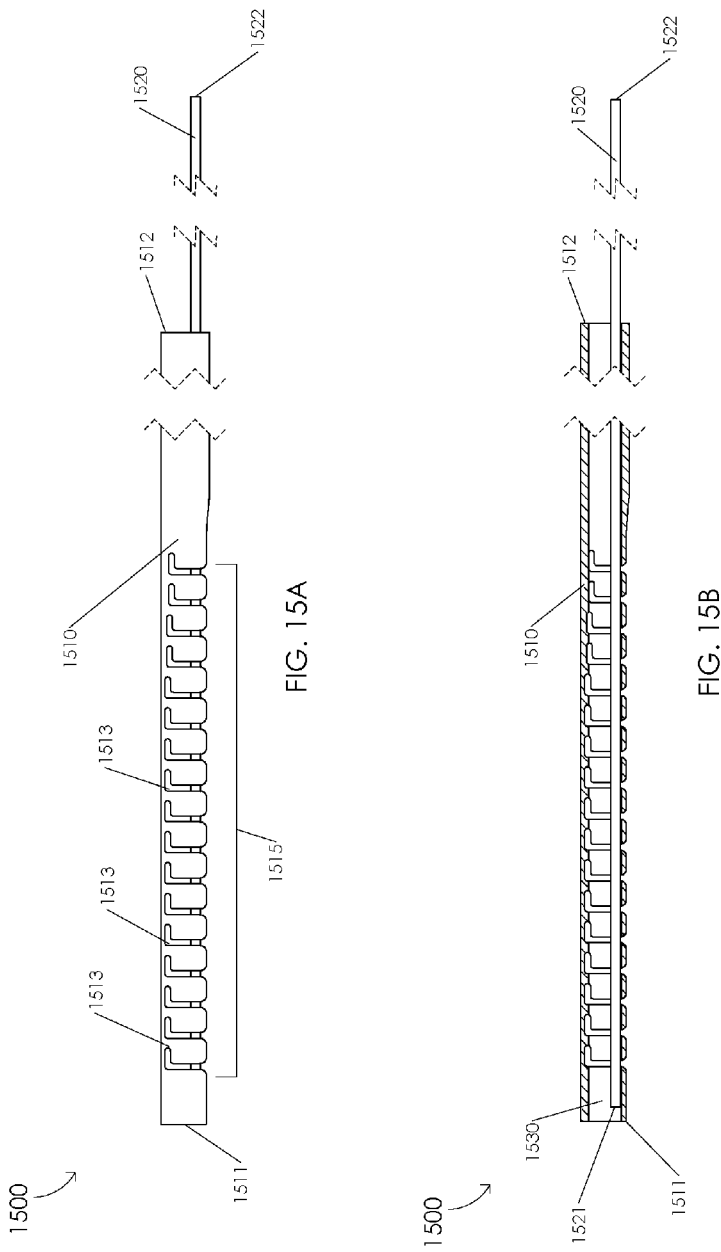

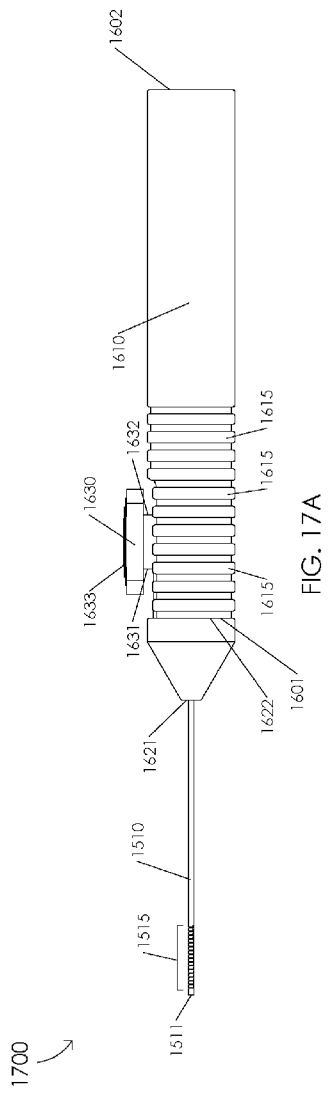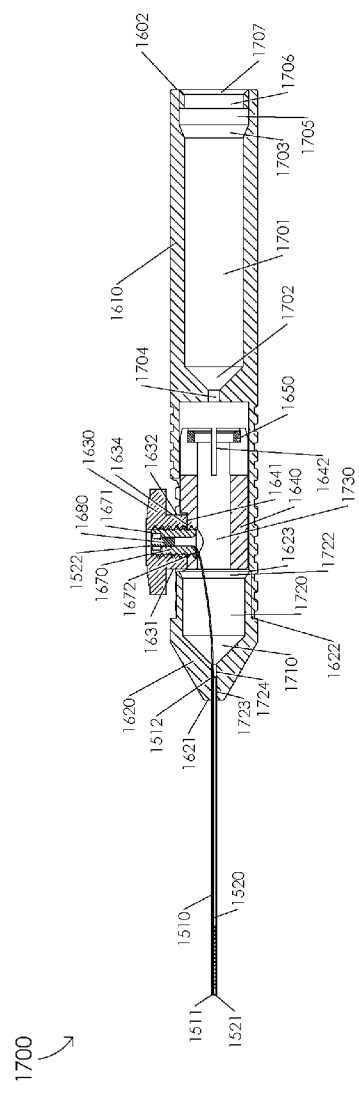

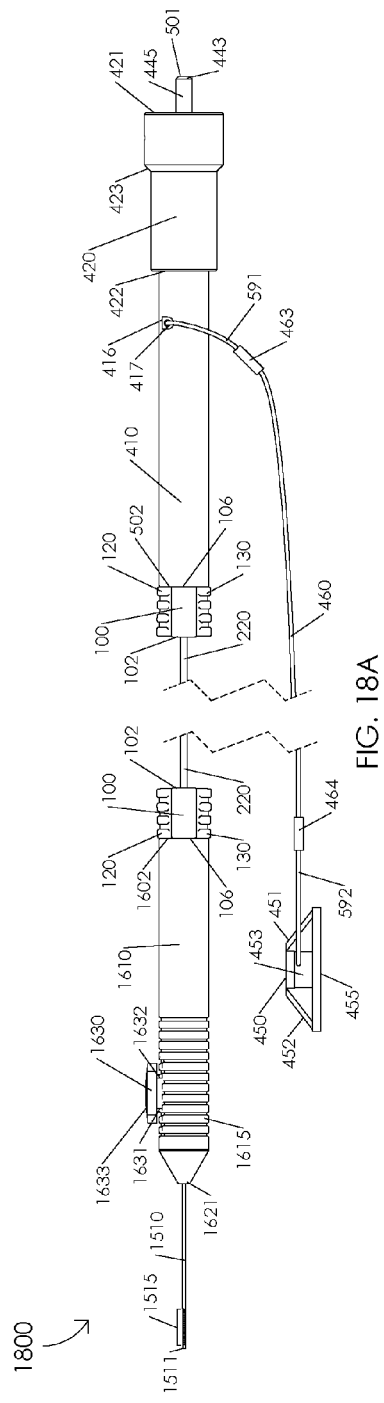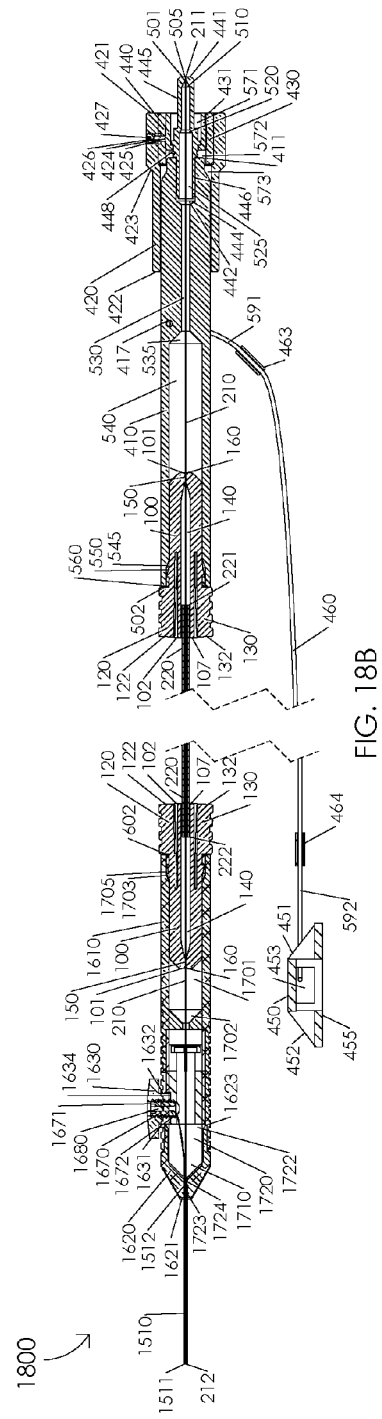
FIG. 18A
FIG. 18B

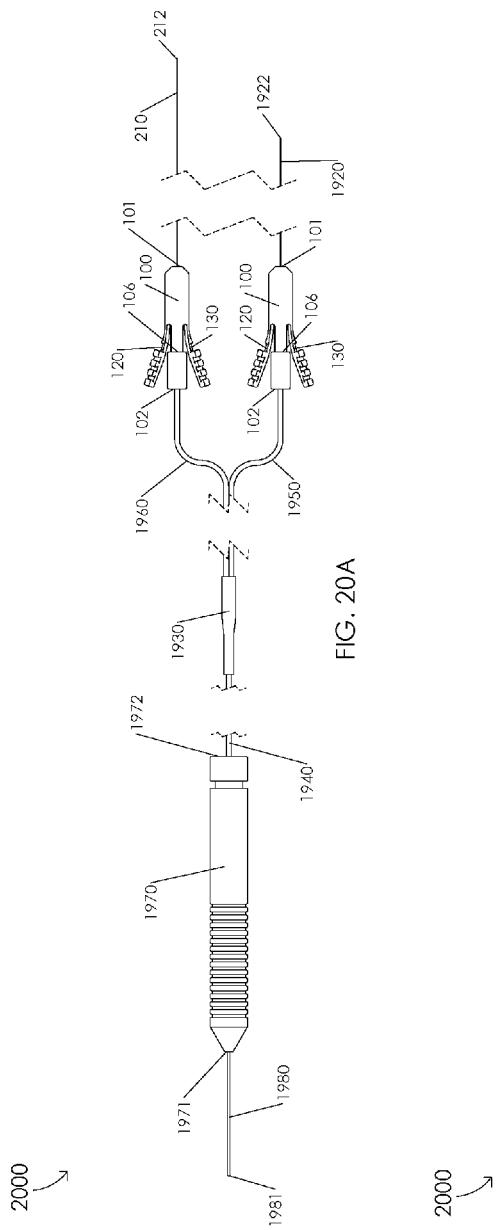
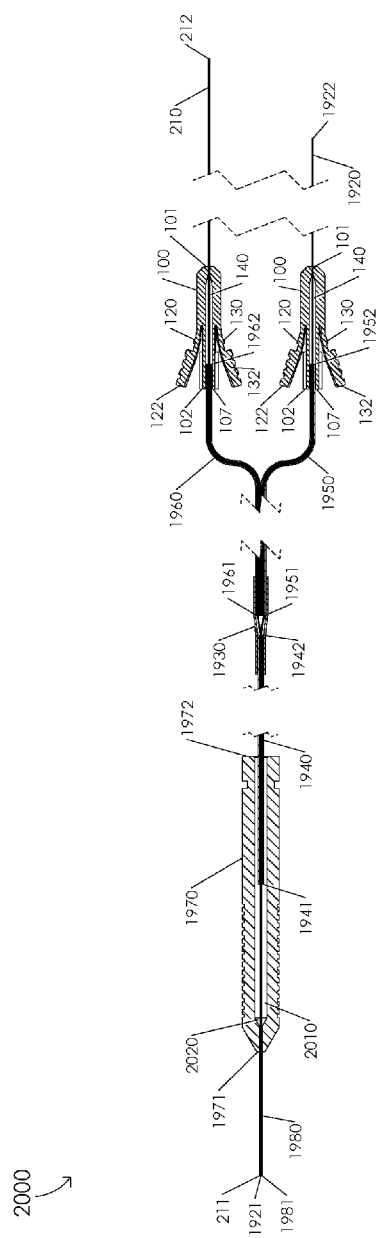
FIG. 20A
FIG. 20B

US 10,245,182 B2

LASER PROBE WITH REPLACEABLE OPTIC FIBERS

CROSS-REFERENCE TO RELATED APPLICATIONS

This application claims the benefit of U.S. Provisional Application No. 62/255,398, filed Nov. 14, 2015.

FIELD OF THE INVENTION

The present disclosure relates to a surgical instrument, and, more particularly, to a laser probe with replaceable optic fibers.

BACKGROUND OF THE INVENTION

A wide variety of ophthalmic procedures require a laser energy source. For example, ophthalmic surgeons may use laser photocoagulation to treat proliferative retinopathy. Proliferative retinopathy is a condition characterized by the development of abnormal blood vessels in the retina that grow into the vitreous humor. Ophthalmic surgeons may treat this condition by energizing a laser to cauterize portions of the retina to prevent the abnormal blood vessels from growing and hemorrhaging. Typically, treatments are performed using a disposable, single-use laser probe connected to a laser surgical machine by an optical fiber. Unfortunately, use of disposable, single-use laser probes increases treatment costs because a new laser probe is required for each surgical treatment. Accordingly, there is a need for a laser probe that may be safely used to perform more than one surgical procedure.

BRIEF SUMMARY OF THE INVENTION

The present disclosure provides a laser probe with replaceable optic fibers. In one or more embodiments, a laser probe with replaceable optic fibers may comprise a handle, an optic fiber fixture, and a replaceable optic fiber. Illustratively, the replaceable optic fiber may comprise an optic fiber having an optic fiber distal end and an optic fiber proximal end. In one or more embodiments, the optic fiber may be disposed in a first transitory connector having a first transitory connector distal end and a first transitory connector proximal end. Illustratively, the optic fiber may be disposed in the first transitory connector wherein the optic fiber distal end extends a fixed distance from the transitory connector distal end. In one or more embodiments, the optic fiber may be disposed in a second transitory connector having a second transitory connector distal end and a second transitory connector proximal end. Illustratively, the optic fiber may be disposed in the second transitory connector wherein the optic fiber proximal end extends a fixed distance from the second transitory connector distal end. In one or more embodiments, the first transitory connector may be inserted in the handle and the second transitory connector may be inserted in the optic fiber fixture.

BRIEF DESCRIPTION OF THE DRAWINGS

The above and further advantages of the present invention may be better understood by referring to the following description in conjunction with the accompanying drawings in which like reference numerals indicate identical or functionally similar elements:

FIGS. 3A and 3B are schematic diagrams illustrating an assembled replaceable fiber;
FIGS. 5A and 5B are schematic diagrams illustrating an assembled optic fiber fixture;
FIGS. 6A and 6B are schematic diagrams illustrating a handle base;
FIGS. 7A and 7B are schematic diagrams illustrating a hypodermic tube;
FIGS. 8A and 8B are schematic diagrams illustrating an exploded view of a handle assembly;
FIGS. 9A and 9B are schematic diagrams illustrating an assembled handle;
FIGS. 15A and 15B are schematic diagrams illustrating an assembled steerable hypodermic tube;
FIGS. 17A, 17B, 17C, and 17D are schematic diagrams illustrating an assembled steerable handle;
FIGS. 18A and 18B are schematic diagrams illustrating an assembled steerable laser probe with replaceable fibers;
FIGS. 20A and 20B are schematic diagrams illustrating an assembled illuminated handle.

DETAILED DESCRIPTION OF AN ILLUSTRATIVE EMBODIMENT

Figure 1A:
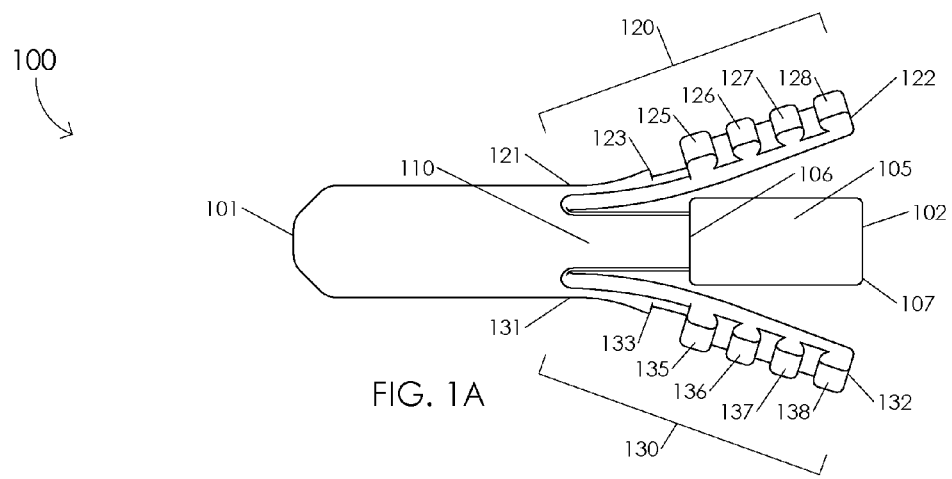
FIGS. 1A and 1B are schematic diagrams illustrating a transitory connector.
Figure 1B:
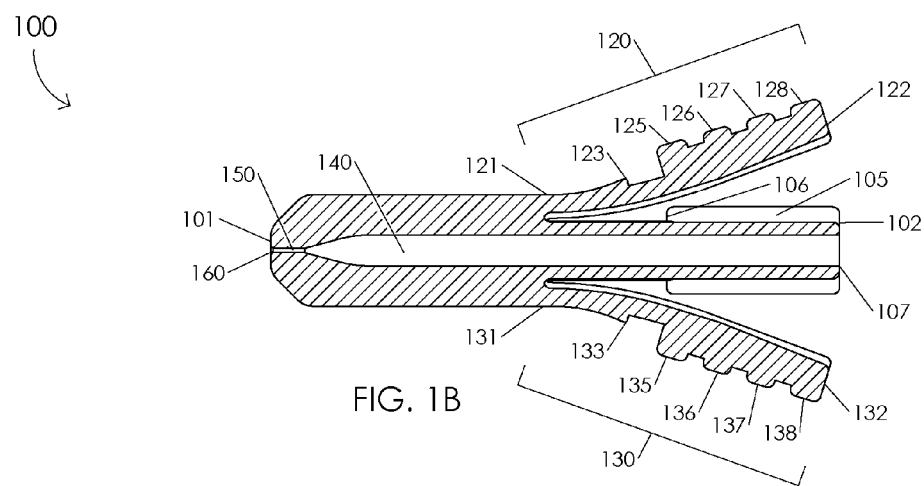

FIGS. 1A and 1B are schematic diagrams illustrating a transitory connector 100. FIG. 1A illustrates a side view of a transitory connector 100. Illustratively, transitory connector 100 may comprise a transitory connector distal end 101, a transitory connector proximal end 102, a proximal base 105, a distal base 110, a superior arm 120, and an inferior arm 130. In one or more embodiments, proximal base 105 may comprise a proximal base distal end 106 and a proximal base proximal end 107. Illustratively, distal base 110 may be disposed between transitory connector distal end 101 and proximal base 105, e.g., distal base 110 may be disposed between transitory connector distal end 101 and proximal base distal end 106. In one or more embodiments, proximal base proximal end 107 may be transitory connector proximal end 102. Illustratively, superior arm 120 may comprise a superior arm distal end 121 and a superior arm proximal end 122. In one or more embodiments, superior arm 120 may comprise a superior arm barb 123, e.g., superior arm 120 may comprise a superior arm barb 123 disposed between superior arm distal end 121 and superior arm proximal end 122. Illustratively, superior arm 120 may comprise a first lateral projection 125, a second lateral projection 126, a third lateral projection 127, and a fourth lateral projection 128. In one or more embodiments, first lateral projection 125 may be disposed between superior arm barb 123 and second lateral projection 126. Illustratively, second lateral projection 126 may be disposed between first lateral projection 125 and third lateral projection 127. In one or more embodiments, third lateral projection 127 may be disposed between second lateral projection 126 and fourth lateral projection 128. Illustratively, fourth lateral projection 128 may be disposed between third lateral projection 127 and superior arm proximal end 122. In one or more embodiments, superior arm 120 may be disposed between transitory connector distal end 101 and transitory connector proximal end 102. Illustratively, inferior arm 130 may comprise an inferior arm distal end 131 and an inferior arm proximal end 132. In one or more embodiments, inferior arm 130 may comprise an inferior arm barb 133, e.g., inferior arm 130 may comprise an inferior arm barb 133 disposed between inferior arm distal end 131 and inferior arm proximal end 132. Illustratively, inferior arm 130 may comprise a first lateral projection 135, a second lateral projection 136, a third lateral projection 137, and a fourth lateral projection 138. In one or more embodiments, first lateral projection 135 may be disposed between inferior arm barb 133 and second lateral projection 136. Illustratively, second lateral projection 136 may be disposed between first lateral projection 135 and third lateral projection 137. In one or more embodiments, third lateral projection 137 may be disposed between second lateral projection 136 and fourth lateral projection 138. Illustratively, fourth lateral projection 138 may be disposed between third lateral projection 137 and inferior arm proximal end 132. In one or more embodiments, inferior arm 130 may be disposed between transitory connector distal end 101 and transitory connector proximal end 102.

FIG. 1B illustrates a cross-sectional view in a sagittal plane of a transitory connector 100. Illustratively, transitory connector 100 may comprise a tapered inner lumen 140, an optic fiber housing 150, and a fixation mechanism housing 160. In one or more embodiments, transitory connector 100 may be manufactured from a material configured to deform if transitory connector 100 is sterilized in a medical autoclave, e.g., transitory connector 100 may be manufactured from a material configured to permanently deform if transitory connector 100 is sterilized in a medical autoclave. Illustratively, transitory connector 100 may be manufactured from a material having a melting point below a temperature parameter for a steam sterilization cycle, e.g., transitory connector 100 may be manufactured from a material having a melting point below a temperature parameter for a gravity-displacement steam sterilization cycle, a dynamic-air-removal steam sterilization cycle, etc. In one or more embodiments, transitory connector 100 may be manufactured from a material having a melting point below 140.0 degrees Fahrenheit. Illustratively, transitory connector 100 may be manufactured from a material having a melting point in a range of 158.0 to 212.0 degrees Fahrenheit, e.g., transitory connector 100 may be manufactured from a material having a melting point of 160.0 degrees Fahrenheit. In one or more embodiments, transitory connector 100 may be manufactured from a material having a melting point of less than 158.0 degrees Fahrenheit or greater than 212.0 degrees Fahrenheit. In one or more embodiments, transitory connector 100 may be manufactured from a material having a melting point below 250.0 degrees Fahrenheit. Illustratively, transitory connector 100 may be manufactured from a material having a melting point below 270.0 degrees Fahrenheit. In one or more embodiments, transitory connector 100 may be manufactured from a material having a melting point below 275.0 degrees Fahrenheit.

Illustratively, transitory connector 100 may be manufactured from a material configured to temporarily deform if transitory connector 100 is sterilized in a medical autoclave, e.g., transitory connector 100 may be manufactured from a material configured to absorb water in a medical autoclave. In one or more embodiments, an absorption of water may be configured to deform transitory connector 100, e.g., an absorption of water may be configured to cause transitory connector 100 to expand. Illustratively, transitory connector 100 may be manufactured from a porous material configured to facilitate a deformation of transitory connector 100 if transitory connector 100 is sterilized in a medical autoclave. In one or more embodiments, transitory connector 100 may be manufactured with one or more cavities configured to facilitate a deformation of transitory connector 100 if transitory connector 100 is sterilized in a medical autoclave. Illustratively, transitory connector 100 may be manufactured from any suitable material, e.g., polymers, metals, metal alloys, etc., or from any combination of suitable materials. In one or more embodiments, transitory connector 100 may be manufactured by a 3D printing process. For example, transitory connector 100 may be manufactured by selective laser sintering, selective heat sintering, selective laser melting, electron-beam melting, direct metal laser sintering, electron beam freeform fabrication, etc. Illustratively, transitory connector 100 may be manufactured by injection molding.

In one or more embodiments, transitory connector 100 may be manufactured from poly(acrylamide), poly(acrylic acid), poly(adipic anhydride), poly(7-aminoenanthic acid), poly(12-aminolauric acid), poly(11-aminoundecanoic acid), poly(azelaic anhydride), poly[1,3-butadiene(1,4-)-alt-methacrylonitrile], poly[1,3-butadiene(1,4-)-alt-methyl methacrylate], poly(butadiene oxide), poly(caprylaldehyde), poly(1,4-cyclohexylenedimethylene azelate), poly(1,4-cyclohexylenedimethylene dodecanedioate), poly(1,4-cyclohexylenedimethylene glutarate), poly(1,4-cyclohexylenedimethylene p-phenylenediacetate), poly(1,4-cyclohexylenedimethylene pimelate), poly(1,4-cyclohexylenedimethylene sebacate), poly(1,4-cyclohexylenedimethylene suberate), poly(cyclohexylidenethiohexamethylene sulfide), poly(cyclopropylenedimethylene piperazinediurethane), poly(cyclopropylidenedimethylene oxide), poly(decamethylene), poly(decamethylene carbonate), poly[(decamethylenedioxy)-dihexamethylene oxide], poly(decamethylene disulfide), poly(decamethylenedithioethylene disulfide), poly(decamethylenedithiohexamethylene disulfide), poly(decamethylene dithioladipate), poly(decamethylenedithiotetramethylene disulfide), poly(decamethylene pimelate), poly(decamethylene fumaramide), poly(decamethylene glutaramide), poly(decamethylene isophthalate), poly(decamethylene malonate), poly(decamethylene oxydiacetate), poly(decamethyleneoxymethylene oxide), poly(decamethylene succinate), poly(decamethylene sulfide), poly(decamethylene thiodivalerate), poly(decamethylenethiohexamethylene sulfide), poly(divinylbenzal), poly(dodecamethylene), poly(dodecanedioic anhydride), poly(eicosamethylene adipate), poly(eicosamethylene azelate), poly(eicosamethylene glutarate), poly(eicosamethylene isophthalate), poly(eicosamethylene malonate), poly(eicosamethylene oxalate), poly(eicosamethylene oxydiacetate), poly(eicosamethylene phthalate), poly(eicosamethylene pimelate), poly(eicosamethylene sebacate), poly(eicosamethylene suberate), poly(eicosamethylene succinate), poly(eicosamethylene thiodivalerate), poly[ethylene p-(carboxyphenoxy)-butyrate], poly[ethylene p-(carboxyphenoxy)caproate], poly[ethylene p-(carboxyphenoxy)-heptanoate], poly[ethylene p(carboxyphenoxy)-undecanoate], poly[ethylene p-(carboxyphenoxy)-valerate], poly(ethylene 2,2'-dibenzoate), poly[(ethylenedioxy)-diethylene 2,2'-dibenzoate], poly(ethylene 2,2'-dibenzoate), poly[(ethylenedioxy)-diethylene 3,3'-dibenzoate], poly[(ethylenedioxy)-diethylene isophthalate], poly[(ethylenedioxy)-diethylene sebacate], poly[(ethylenedioxy)-diethylene thiodivalerate], poly(ethylene di siloxanylenedipropionami de), poly[(ethylenedithio)-diacetic anhydride], poly[(ethylenedithio)dipropionic anhydride], poly(ethylene dithionisophthalate), poly(ethelene dithiotetramethylene disulfide), poly(ethylene fumaramide), poly(ethylene glutarate), poly(ethylene 2,4-hexadienediamide), poly(ethylene phthalate), poly(ethylene sulfonyldivalerate), poly(ethylene terephthalate), poly(heptamethylene), poly(hexamethylene azelate), poly(hexamethylene carbonate), poly[hexamethylene p-(carboxyphenoxy)-acetate], poly[hexamethylene p-(carboxyphenoxy)-caproate], poly[hexamethylene p(carboxyphenoxy)-undecanoate], poly[hexamethylene p-(carboxyphenoxy)-valerate], poly(hexamethylene isophthalate), poly[hexamethylene (methylene-2,5-tetrahydrofuran)dicarboxamide], poly(hexamethylene octadecanediamide), poly(hexamethylene oxydiacetate), poly(hexamethylene 4,4'-oxydibenzoate), poly(hexamethylene pimelate), poly(hexamethylene succinate), poly(hexamethylene thiodivalerate), poly(hexamethylenethiooentamethylene sulfide), poly(hexamethylenethiotetramethylene sulfide), poly(hexenamer), etc. Illustratively, transitory connector 100 may be manufactured from any substituted polymers of poly(acrylamide), poly(acrylic acid), poly(adipic anhydride), poly(7-aminoenanthic acid), poly(12-aminolauric acid), poly(11-aminoundecanoic acid), poly(azelaic anhydride), poly[1,3-butadiene(1,4-)-alt-methacrylonitrile], poly[1,3-butadiene(1,4-)-alt-methyl methacrylate], poly(butadiene oxide), poly(caprylaldehyde), poly(1,4-cyclohexylenedimethylene azelate), poly(1,4-cyclohexylenedimethylene dodecanedioate), poly(1,4-cyclohexylenedimethylene glutarate), poly(1,4-cyclohexylenedimethylene p-phenylenediacetate), poly(1,4-cyclohexylenedimethylene pimelate), poly(1,4-cyclohexylenedimethylene sebacate), poly(1,4-cyclohexylenedimethylene suberate), poly(cyclohexylidenethiohexamethylene sulfide), poly(cyclopropylenedimethylene piperazinediurethane), poly(cyclopropylidenedimethylene oxide), poly(decamethylene), poly(decamethylene carbonate), poly[(decamethylenedioxy)-dihexamethylene oxide], poly(decamethylene disulfide), poly(decamethylenedithioethylene disulfide), poly(decamethylenedithiohexamethylene disulfide), poly(decamethylene dithioladipate), poly(decamethylenedithiotetramethylene disulfide), poly(decamethylene pimelate), poly(decamethylene fumaramide), poly(decamethylene glutaramide), poly(decamethylene isophthalate), poly(decamethylene malonate), poly(decamethylene oxydiacetate), poly(decamethyleneoxymethylene oxide), poly(decamethylene succinate), poly(decamethylene sulfide), poly(decamethylene thiodivalerate), poly(decamethylenethiohexamethylene sulfide), poly(divinylbenzal), poly(dodecamethylene), poly(dodecanedioic anhydride), poly(eicosamethylene adipate), poly(eicosamethylene azelate), poly(eicosamethylene glutarate), poly(eicosamethylene isophthalate), poly(eicosamethylene malonate), poly(eicosamethylene oxalate), poly(eicosamethylene oxydiacetate), poly(eicosamethylene phthalate), poly(eicosamethylene pimelate), poly(eicosamethylene sebacate), poly(eicosamethylene suberate), poly(eicosamethylene succinate), poly(eicosamethylene thiodivalerate), poly[ethylene p-(carboxyphenoxy)-butyrate], poly[ethylene p-(carboxyphenoxy)caproate], poly[ethylene p-(carboxyphenoxy)-heptanoate], poly[ethylene p(carboxyphenoxy)-undecanoate], poly[ethylene p-(carboxyphenoxy)-valerate], poly(ethylene 2,2'-dibenzoate), poly[(ethylenedioxy)-diethylene 2,2'-dibenzoate], poly(ethylene 2,2'-dibenzoate), poly[(ethylenedioxy)-diethylene 3,3'-dibenzoate], poly[(ethylenedioxy)-diethylene isophthalate], poly[(ethylenedioxy)-diethylene sebacate], poly[(ethylenedioxy)-diethylene thiodivalerate], poly(ethylene di siloxanylenedipropionami de), poly[(ethylenedithio)-diacetic anhydride], poly[(ethylenedithio)dipropionic anhydride], poly(ethylene dithionisophthalate), poly(ethelene dithiotetramethylene disulfide), poly(ethylene fumaramide), poly(ethylene glutarate), poly(ethylene 2,4-hexadienediamide), poly(ethylene phthalate), poly(ethylene sulfonyldivalerate), poly(ethylene terephthalate), poly(heptamethylene), poly(hexamethylene azelate), poly(hexamethylene carbonate), poly[hexamethylene p-(carboxyphenoxy)-acetate], poly[hexamethylene p-(carboxyphenoxy)-caproate], poly[hexamethylene p-(carboxyphenoxy)-undecanoate], poly[hexamethylene p-(carboxyphenoxy)-valerate], poly(hexamethylene isophthalate), poly[hexamethylene (methylene-2,5-tetrahydrofuran)dicarboxamide], poly(hexamethylene octadecanediamide), poly(hexamethylene oxydiacetate), poly(hexamethylene 4,4'-oxydibenzoate), poly(hexamethylene pimelate), poly(hexamethylene succinate), poly(hexamethylene thiodivalerate), poly(hexamethylenethiooentamethylene sulfide), poly(hexamethylenethiotetramethylene sulfide), poly(hexenamer), etc.

Figure 2:
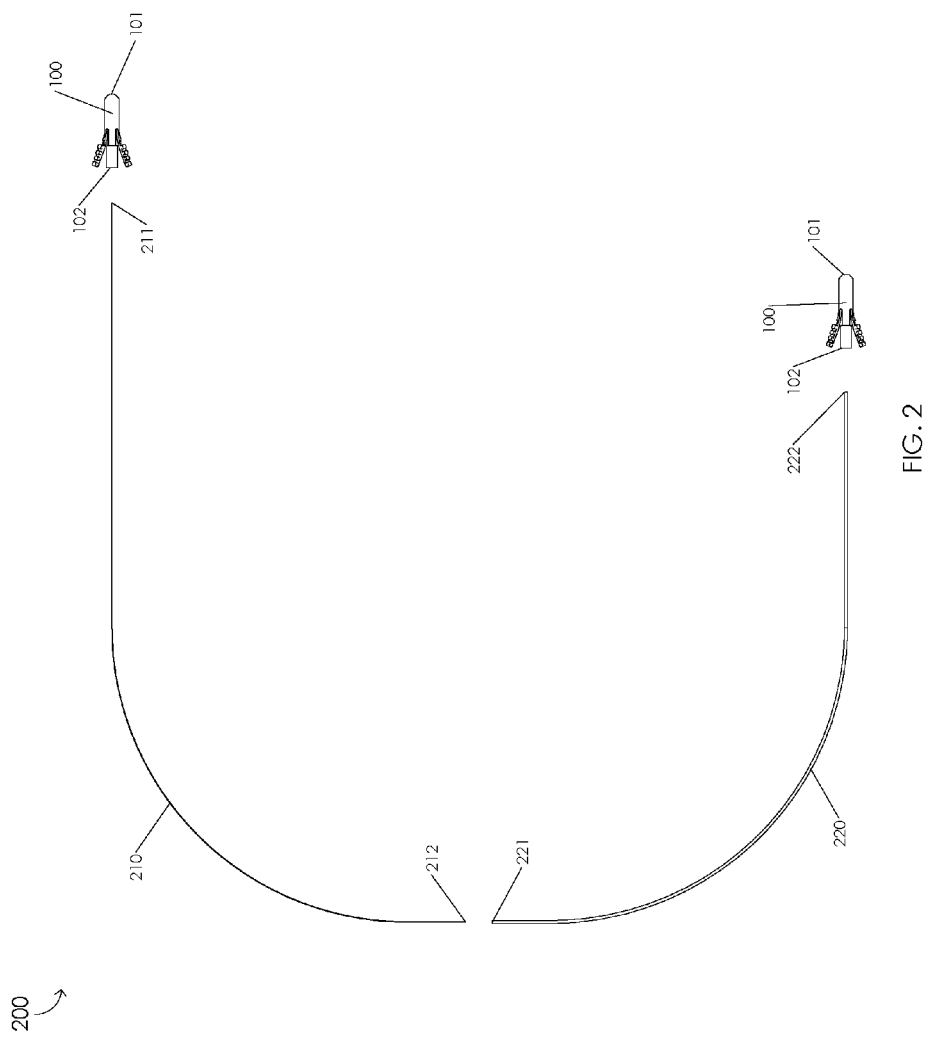
FIG. 2 is a schematic diagram illustrating an exploded view of a replaceable fiber assembly.

FIG. 2 is a schematic diagram illustrating an exploded view of a replaceable fiber assembly 200. Illustratively, a replaceable fiber assembly 200 may comprise a first transitory connector 100, an optic fiber 210, jacketing 220, and a second transitory connector 100. In one or more embodiments, optic fiber 210 may comprise an optic fiber distal end 211 and an optic fiber proximal end 212. Illustratively, optic fiber 210 may be configured to transmit laser light. In one or more embodiments, jacketing 220 may comprise a jacketing distal end 221 and a jacketing proximal end 222. Illustratively, jacketing 220 may be manufactured from any suitable material, e.g., polymers, metals, metal alloys, etc., or from any combination of suitable materials.

FIGS. 3A and 3B are schematic diagrams illustrating an assembled replaceable fiber 300. FIG. 3A illustrates a side view of an assembled replaceable fiber 300. In one or more embodiments, optic fiber distal end 211 may extend a distance from first transitory connector distal end 101. Illustratively, optic fiber proximal end 212 may extend a distance from second transitory connector distal end 101. FIG. 3B illustrates a cross-sectional view in a sagittal plane of an assembled replaceable fiber 300. Illustratively, optic fiber 210 may be disposed within jacketing 220 wherein optic fiber distal end 211 extends a distance from jacketing distal end 221 and wherein optic fiber proximal end 212 extends a distance from jacketing proximal end 222. In one or more embodiments, a portion of jacketing 220 may be disposed in a portion of first transitory connector 100, e.g., jacketing distal end 221 may be disposed in tapered inner lumen 140. Illustratively, a portion of jacketing 220 may be fixed in a portion of first transitory connector 100, e.g., a portion of jacketing 220 may be fixed in a portion of first transitory connector 100 by an adhesive, a friction fit, a crimp, a tie, a weld, etc. In one or more embodiments, a portion of jacketing 220 may be disposed in a portion of second transitory connector 100, e.g., jacketing proximal end 222 may be disposed in tapered inner lumen 140. Illustratively, a portion of jacketing 220 may be fixed in a portion of second transitory connector 100, e.g., a portion of jacketing 220 may be fixed in a portion of second transitory connector 100 by an adhesive, a friction fit, a crimp, a tie, a weld, etc.

In one or more embodiments, optic fiber 210 may be disposed in first transitory connector 100 wherein optic fiber 210 is disposed in tapered inner lumen 140, optic fiber housing 150, and fixation mechanism housing 160. Illustratively, a portion of optic fiber 210 may be fixed within fixation mechanism housing 160, e.g., a portion of optic fiber 210 may be fixed within fixation mechanism housing 160 by an adhesive, a friction fit, a crimp, a tie, a weld, etc. In one or more embodiments, optic fiber 210 may be fixed in first transitory connector 100 wherein optic fiber distal end 211 extends a fixed distance from first transitory connector distal end 101. Illustratively, optic fiber 210 may be disposed in second transitory connector 100 wherein optic fiber 210 is disposed in tapered inner lumen 140, optic fiber housing 150, and fixation mechanism housing 160. Illustratively, a portion of optic fiber 210 may be fixed within fixation mechanism housing 160, e.g., a portion of optic fiber 210 may be fixed within fixation mechanism housing 160 by an adhesive, a friction fit, a crimp, a tie, a weld, etc. In one or more embodiments, optic fiber 210 may be fixed in second transitory connector 100 wherein optic fiber proximal end 212 extends a fixed distance from second transitory connector distal end 101. Illustratively, a distance that optic fiber distal end 211 extends from first transitory connector distal end 101 may be identical to a distance that optic fiber proximal end 212 extends from second transitory connector distal end 101. In one or more embodiments, a distance that optic fiber distal end 211 extends from first transitory connector distal end 101 and a distance that optic fiber proximal end 212 extends from second transitory connector distal end 101 may be configured to allow first transitory connector 100 and second transitory connector 100 to be interchangeable.

Figure 4:
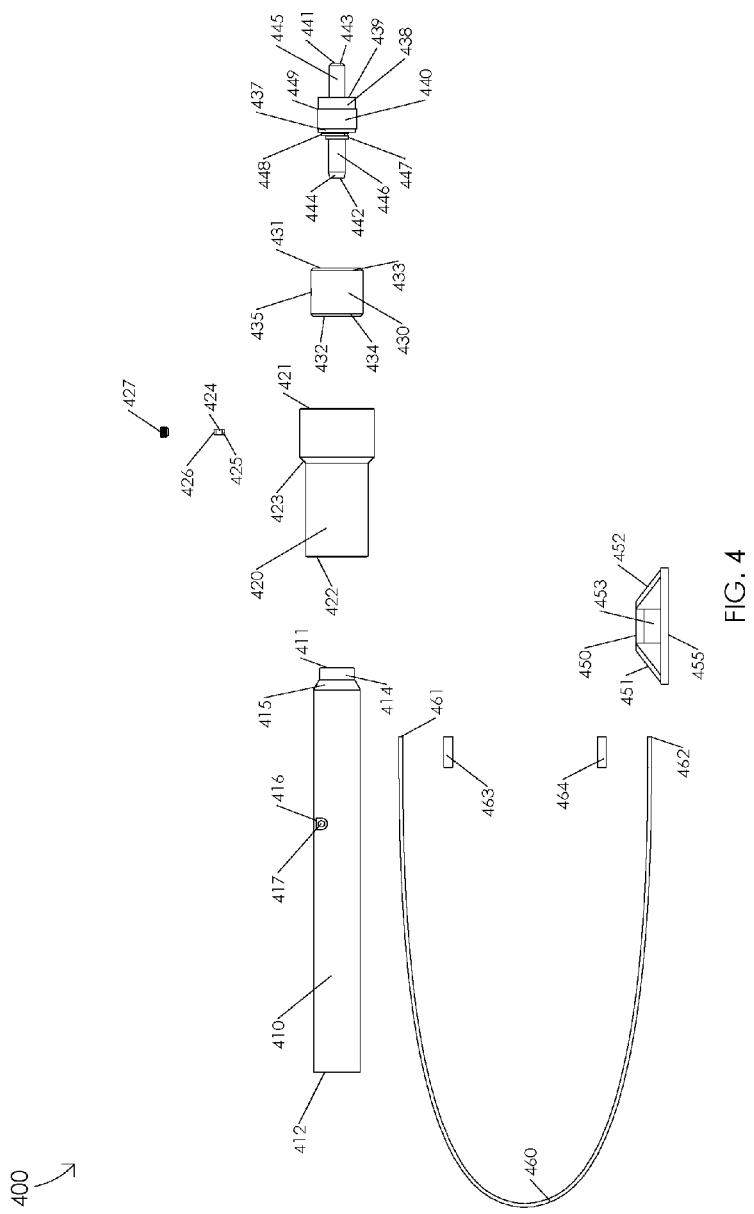
FIG. 4 is a schematic diagram illustrating an exploded view of an optic fiber fixture assembly.

FIG. 4 is a schematic diagram illustrating an exploded view of an optic fiber fixture assembly 400. Illustratively, an optic fiber fixture assembly 400 may comprise a fixture base 410, a machine connector housing 420, an electrical element 424, a fixation mechanism 427, an extender 430, a machine connector 440, a machine coupler 450, a lanyard cable 460, a distal fastener 463, and a proximal fastener 464. In one or more embodiments, fixture base 410 may comprise a fixture base distal end 411 and a fixture base proximal end 412. Illustratively, fixture base 410 may comprise an extender interface 414, a fixture base distal taper 415, an indentation 416, and a lanyard cable guide 417. In one or more embodiments, lanyard cable guide 417 may be disposed in indentation 416. Illustratively, lanyard cable guide 417 may be disposed dorsally in fixture base 410. In one or more embodiments, machine connector housing 420 may comprise a machine connector housing distal end 421 and a machine connector housing proximal end 422. Illustratively, machine connector housing 420 may comprise a machine connector housing taper 423. In one or more embodiments, extender 430 may comprise an extender distal end 431 and an extender proximal end 432. Illustratively, extender 430 may comprise an extender distal taper 433 and an extender proximal taper 434. In one or more embodiments, extender 430 may comprise an electrical element housing 435. Illustratively, electrical element housing 435 may be configured to house electrical element 424. In one or more embodiments, electrical element 424 may comprise an electrical element inferior end 425 and an electrical element superior end 426.

In one or more embodiments, machine connector 440 may comprise a machine connector distal end 441 and a machine connector proximal end 442. Illustratively, machine connector 440 may comprise a machine connector distal taper 443, a machine connector proximal taper 444, a distal ferrule 445, and a proximal ferrule 446. In one or more embodiments, machine connector 440 may comprise a machine connector base 438. Illustratively, machine connector base 438 may comprise a machine connector base distal end 439 and a machine connector base proximal end 449. In one or more embodiments, machine connector 440 may comprise a retaining ring distal interface 437, a retaining ring proximal interface 447, and a retaining ring 448. Illustratively, retaining ring 448 may be disposed between retaining ring distal interface 437 and retaining ring proximal interface 447. In one or more embodiments, lanyard cable 460 may comprise a lanyard cable distal end 461 and a lanyard cable proximal end 462. Illustratively, machine coupler 450 may comprise a machine coupler inferior end 451 and a machine coupler superior end 452. In one or more embodiments, machine coupler 450 may comprise a machine coupler aperture 453. Illustratively, machine coupler 450 may comprise a machine interface 455.

FIGS. 5A and 5B are schematic diagrams illustrating an assembled optic fiber fixture 500. FIG. 5A illustrates a side view of an assembled optic fiber fixture 500. FIG. 5B illustrates a cross-sectional view in a sagittal plane of an assembled optic fiber fixture 500. Illustratively, an assembled optic fiber fixture 500 may comprise an assembled optic fiber fixture distal end 501 and an assembled optic fiber fixture proximal end 502. In one or more embodiments, assembled optic fiber fixture 500 may comprise an optic fiber proximal end guide 505, an inner lumen distal taper 510, a machine connector distal inner lumen 515, an inner lumen proximal taper 520, a machine connector proximal inner lumen 525, a fixture base inner bore 530, a transitory connector proximal housing distal taper 535, a transitory connector proximal housing 540, a transitory connector proximal housing proximal taper 545, a proximal barb interface 550, a proximal arm interface 555, and a fixture base inner taper 560.

In one or more embodiments, lanyard cable 460 may comprise a distal loop 591 and a proximal loop 592. Illustratively, distal fastener 463 may be disposed over a portion of lanyard cable 460 wherein lanyard cable distal end 461 extends a distance from distal fastener 463. In one or more embodiments, lanyard cable distal end 461 may be threaded through lanyard cable guide 417 and into a portion of distal fastener 463 to form distal loop 591. Illustratively, distal fastener 463 may be configured to fix lanyard cable distal end 461 within distal fastener 463, e.g., distal fastener 463 may be configured to fix lanyard cable distal end 461 within distal fastener 463 by an adhesive, a crimp, a weld, a friction fit, etc. In one or more embodiments, proximal fastener 464 may be disposed over a portion of lanyard cable 460 wherein lanyard cable proximal end 462 extends a distance from proximal fastener 464. Illustratively, lanyard cable proximal end 462 may be threaded through machine coupler aperture 453 and into a portion of proximal fastener 464 to form proximal loop 592. In one or more embodiments, proximal fastener 464 may be configured to fix lanyard cable proximal end 462 within proximal fastener 464, e.g., proximal fastener 464 may be configured to fix lanyard cable proximal end 462 within proximal fastener 464 by an adhesive, a crimp, a weld, a friction fit, etc.

Illustratively, machine connector 440 may comprise a machine connector inner chamber 571. In one or more embodiments, distal ferrule 445 may extend a distance out from machine connector inner chamber 571. Illustratively, extender 430 may comprise an extender inner chamber 572. In one or more embodiments, machine connector 440 may be disposed in extender inner chamber 572. Illustratively, machine connector 440 may be disposed in extender 430, e.g., machine connector 440 may be disposed in extender 430 wherein machine connector distal end 441 may extend a distance from extender distal end 431 and wherein machine connector proximal end 442 may extend a distance from extender proximal end 432. In one or more embodiments, machine connector 440 may be fixed in extender 430, e.g., machine connector 440 may be fixed in extender 430 by an adhesive, a crimp, a weld, a friction fit, etc. Illustratively, machine connector housing 420 may comprise a machine connector housing inner chamber 573. In one or more embodiments, extender 430 may be disposed in machine connector housing inner chamber 573. Illustratively, extender 430 may be disposed in machine connector housing 420, e.g., extender 430 may be disposed in machine connector housing 420 wherein extender distal end 431 is disposed between machine connector housing distal end 421 and machine connector housing proximal end 422 and wherein extender proximal end 432 is disposed between machine connector housing distal end 421 and machine connector housing proximal end 422. In one or more embodiments, extender 430 may be disposed in machine connector housing 420 wherein machine connector distal end 441 extends a distance from machine connector housing distal end 421, e.g., extender may be disposed in machine connector housing 420 wherein machine connector proximal end 442 may be disposed between machine connector housing distal end 421 and machine connector housing proximal end 422. Illustratively, extender 430 may be fixed in machine connector housing 420, e.g., extender 430 may be fixed in machine connector housing 420 by an adhesive, a crimp, a weld, a friction fit, etc.

In one or more embodiments, fixture base 410 may be disposed in machine connector housing 420, e.g., fixture base 410 may be disposed in machine connector housing 420 wherein fixture base proximal end 412 extends a distance from machine connector housing proximal end 422 and wherein fixture base distal end 411 is disposed between machine connector housing distal end 421 and machine connector housing proximal end 422. Illustratively, fixture base 410 may be fixed in machine connector housing 420, e.g., fixture base 410 may be fixed in machine connector housing 420 by an adhesive, a crimp, a weld, a friction fit, etc. In one or more embodiments, fixture base 410 may be disposed in extender 430, e.g., fixture base 410 may be disposed in extender 430 wherein fixture base proximal end 412 extends a distance from extender proximal end 432 and wherein fixture base distal end 411 is disposed between extender distal end 431 and extender proximal end 432. Illustratively, fixture base 410 may be fixed in extender 430, e.g., fixture base 410 may be fixed in extender 430 by an adhesive, a crimp, a weld, a friction fit, etc. In one or more embodiments, machine connector 440 may be disposed in fixture base 410, e.g., machine connector 440 may be disposed in fixture base 410 wherein machine connector distal end 441 extends a distance from fixture base distal end 411 and wherein machine connector proximal end 442 is disposed between fixture base distal end 411 and fixture base proximal end 412. Illustratively, machine connector 440 may be fixed in fixture base 410, e.g., machine connector 440 may be fixed in fixture base 410 by an adhesive, a crimp, a weld, a friction fit, etc.

In one or more embodiments, electrical element 424 may be disposed in machine connector housing 420 and extender 430, e.g., electrical element may be disposed in electrical element housing 435. Illustratively, electrical element 424 may be fixed in electrical element housing 435, e.g., electrical element 424 may be fixed in electrical element housing 435 by an adhesive, a crimp, a weld, a friction fit, etc. In one or more embodiments, electrical element 424 may be disposed in machine connector housing 420 and extender 430 wherein electrical element inferior end 425 may be in contact with machine connector 440, e.g., electrical element 424 may be disposed in electrical element housing 435 wherein electrical element inferior end 425 may be in contact with machine connector 440. Illustratively, electrical element 424 may be electrically connected to machine connector 440. In one or more embodiments, electrical element 424 may be configured to convey data to a machine, e.g., electrical element 424 may be configured to convey data to a laser machine. Illustratively, electrical element 424 may comprise a resistor, e.g., electrical element 424 may comprise a cylindrical resistor. In one or more embodiments, electrical element 424 may comprise a radio frequency identification chip.

Illustratively, fixation mechanism 427 may be disposed in machine connector housing 420, e.g., fixation mechanism 427 may be disposed in machine connector housing 420 wherein a portion of fixation mechanism 427 contacts a portion of electrical element 424. In one or more embodiments, fixation mechanism 427 may be fixed in machine connector housing 420, e.g., fixation mechanism 427 may be fixed in machine connector housing 420 by an adhesive, a crimp, a weld, a friction fit, etc. Illustratively, fixation mechanism 427 may be configured to fix electrical element 424 in electrical element housing 435, e.g., fixation mechanism 427 may comprise a setscrew configured to fix electrical element 424 in electrical element housing 435. In one or more embodiments, fixation mechanism 427 may be electrically conductive. Illustratively, fixation mechanism 427 may be disposed in machine connector housing 420 wherein fixation mechanism 427 contacts electrical element 424 and electrical element 424 contacts machine connector 440, e.g., fixation mechanism 427 may be disposed in machine connector housing 420 wherein fixation mechanism 427 contacts electrical element superior end 426 and electrical element inferior end 425 contacts machine connector 440. In one or more embodiments, fixation mechanism 427 may be disposed in machine connector housing 420 wherein fixation mechanism 427 is electrically connected to electrical element 424 and electrical element 424 is electrically connected to machine connector 440.

Illustratively, machine coupler 450 may be configured to attach assembled optic fiber fixture 500 to a laser machine, e.g., machine interface 455 may be configured to attach assembled optic fiber fixture 500 to a laser machine. In one or more embodiments, machine interface 455 may comprise a magnet configured to attach assembled optic fiber fixture 500 to a laser machine. Illustratively, machine interface 455 may comprise an adhesive configured to attach assembled optic fiber fixture 500 to a laser machine. In one or more embodiments, assembled optic fiber fixture 500 may be reusable, e.g., assembled optic fiber fixture 500 may be sold non-sterile and not intended to be sterilized by a user in a medical autoclave. Illustratively, a user may clean assembled optic fiber fixture 500 by flushing assembled optic fiber fixture 500 with a syringe of isopropyl alcohol. In one or more embodiments, flushing assembled optic fiber fixture 500 with a syringe of isopropyl alcohol before each use of assembled optic fiber fixture 500 may be configured to remove any particulate matter that may have accumulated in assembled optic fiber fixture 500 since a previous use of assembled optic fiber fixture 500. Illustratively, optic fiber fixture 500 may comprise an end cap configured to fit over optic fiber fixture proximal end 502, e.g., optic fiber fixture 500 may comprise an end cap configured to fit over optic fiber fixture proximal end 502 to prevent particulate matter from accumulating in optic fiber fixture 500 when optic fiber fixture 500 is not being used by a user.

FIGS. 6A and 6B are schematic diagrams illustrating a handle base 600. FIG. 6A illustrates a side view of a handle base 600. Illustratively, handle base 600 may comprise a handle base distal end 601 and a handle base proximal end 602. In one or more embodiments, handle base 600 may comprise a handle base foundation 610. Illustratively, handle base 600 may comprise a plurality of handle base grip points 620. In one or more embodiments, a plurality of handle grip points 620 may be configured to increase a surface area of a handle base 600. FIG. 6B illustrates a cross-sectional view in a sagittal plane of a handle base 600. Illustratively, handle base 600 may comprise a hypodermic tube housing 630, an optic fiber guide 640, a transitory connector distal housing distal taper 650, and a transitory connector distal housing 660. In one or more embodiments, handle base 600 may comprise a transitory connector distal housing proximal taper 665, a distal barb interface 670, a distal arm interface 675, and a handle base inner taper 680.

FIGS. 7A and 7B are schematic diagrams illustrating a hypodermic tube 700. FIG. 7A illustrates a side view of a hypodermic tube 700. Illustratively, hypodermic tube 700 may comprise a hypodermic tube distal end 701 and a hypodermic tube proximal end 702. FIG. 7B illustrates a cross-sectional view in a sagittal plane of a hypodermic tube 700. Illustratively, hypodermic tube 700 may comprise a hypodermic tube through lumen 710, a hypodermic tube distal taper 720, and a hypodermic tube proximal taper 730. Illustratively, hypodermic tube 700 may be manufactured from any suitable material, e.g., polymers, metals, metal alloys, etc., or from any combination of suitable materials.

FIGS. 8A and 8B are schematic diagrams illustrating an exploded view of a handle assembly 800. FIG. 8A illustrates a side view of a handle assembly 800. FIG. 8B illustrates a cross-sectional view in a sagittal plane of a handle assembly 800. Illustratively, a handle assembly 800 may comprise a handle base 600 and a hypodermic tube 700. FIGS. 9A and 9B are schematic diagrams illustrating an assembled handle 900. FIG. 9A illustrates a side view of an assembled handle 900. FIG. 9B illustrates a cross-sectional view in a sagittal plane of an assembled handle 900. Illustratively, a portion of hypodermic tube 700 may be disposed in a portion of handle base 600, e.g., hypodermic tube proximal end 702 may be disposed in hypodermic tube housing 630. In one or more embodiments, hypodermic tube 700 may be fixed in hypodermic tube housing 630, e.g., hypodermic tube 700 may be fixed in hypodermic tube housing 630 by an adhesive, a crimp, a weld, a friction fit, etc.

Figure 10A:
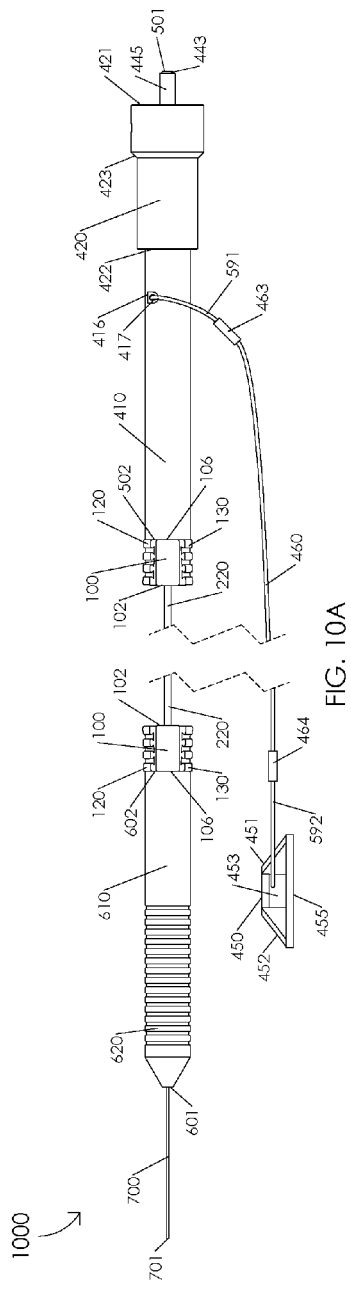
FIGS. 10A and 10B are schematic diagrams illustrating an assembled straight laser probe with replaceable optic fibers.
Figure 10B:
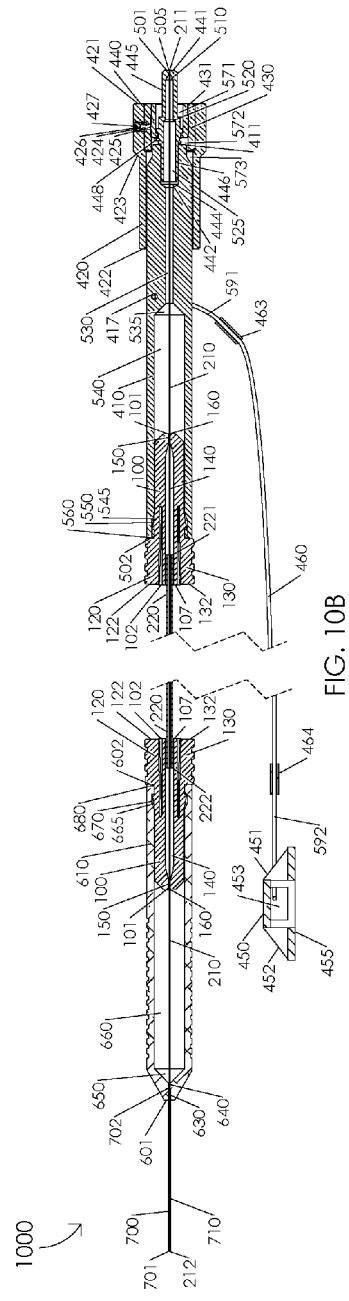

FIGS. 10A and 10B are schematic diagrams illustrating an assembled straight laser probe with replaceable optic fibers 1000. FIG. 10A illustrates a side view of an assembled straight laser probe with replaceable optic fibers 1000. FIG. 10B illustrates a cross-sectional view in a sagittal plane of an assembled straight laser probe with replaceable optic fibers 1000. Illustratively, an assembled straight laser probe with replaceable optic fibers 1000 may comprise an assembled replaceable fiber 300, an assembled handle 900, and an assembled optic fiber fixture 500. In one or more embodiments, a portion of a first transitory connector 100 may be disposed in assembled handle 900, e.g., first transitory connector distal end 101 may be disposed in transitory connector distal housing 660. Illustratively, a portion of first transitory connector 100 may extend a distance from handle base proximal end 602, e.g., first transitory connector proximal end 102 may extend a distance from handle base proximal end 602. In one or more embodiments, a portion of first transitory connector 100 may be disposed in assembled handle 900 wherein superior arm barb 123 is disposed in distal barb interface 670 and inferior arm barb 133 is disposed in distal barb interface 670. Illustratively, a portion of first transitory connector 100 may be disposed in assembled handle 900 wherein superior arm barb 123 is in contact with an outer perimeter of distal barb interface 670 and wherein inferior arm barb 133 is in contact with the outer perimeter of distal barb interface 670. In one or more embodiments, a portion of first transitory connector 100 may be disposed in assembled handle 900 wherein superior arm 120 and inferior arm 130 are disposed in distal arm interface 675. Illustratively, a portion of first transitory connector 100 may be disposed in assembled handle 900 wherein superior arm 120 is in contact with an outer perimeter of distal arm interface 675 and wherein inferior arm 130 is in contact with the outer perimeter of distal arm interface 675. In one or more embodiments, transitory connector distal housing proximal taper 665 may be configured to prevent superior arm barb 123 and inferior arm barb 133 from advancing into transitory connector distal housing 660, e.g., a portion of superior arm barb 123 and a portion of inferior arm barb 133 may contact an outer perimeter of transitory connector distal housing proximal taper 665.

Illustratively, inserting a portion of first transitory connector 100 into transitory connector distal housing 660 may be configured to ingress optic fiber distal end 211 into transitory connector distal housing distal taper 650. In one or more embodiments, transitory connector distal housing distal taper 650 may be configured to guide an ingress of optic fiber distal end 211 into optic fiber guide 640. Illustratively, hypodermic tube proximal taper 730 may be configured to guide an ingress of optic fiber distal end 211 into hypodermic tube through lumen 710. In one or more embodiments, a distance that optic fiber distal end 211 extends from first transitory connector distal end 101 may be configured to cause optic fiber distal end 211 to be adjacent to hypodermic tube distal end 701 when first transitory connector 100 is inserted into transitory connector distal housing 660. Illustratively, hypodermic tube distal taper 720 may be configured to prevent degradation to a laser spot wherein optic fiber distal end 211 is recessed from hypodermic tube distal end 701 relative to a laser spot wherein optic fiber distal end 211 is coplanar with hypodermic tube distal end 701. In one or more embodiments, hypodermic tube distal taper 720 may be configured to ensure that a power output wherein optic fiber distal end 211 is recessed relative to hypodermic tube distal end 701 is identical to a power output wherein optic fiber distal end 211 is coplanar with hypodermic tube distal end 701. Illustratively, hypodermic tube distal taper 720 may be configured to ensure that a laser spot size wherein optic fiber distal end 211 is recessed relative to hypodermic tube distal end 701 is identical to a laser spot size wherein optic fiber distal end 211 is coplanar with hypodermic tube distal end 701. In one or more embodiments, hypodermic tube distal taper 720 may be configured to ensure that a laser spot shape wherein optic fiber distal end 211 is recessed relative to hypodermic tube distal end 701 is identical to a laser spot shape wherein optic fiber distal end 211 is coplanar with hypodermic tube distal end 701.

In one or more embodiments, a portion of a second transitory connector 100 may be disposed in assembled optic fiber fixture 500, e.g., second transitory connector distal end 101 may be disposed in transitory connector proximal housing 540. Illustratively, a portion of second transitory connector 100 may extend a distance from assembled optic fiber fixture proximal end 502, e.g., second transitory connector proximal end 102 may extend a distance from assembled optic fiber fixture proximal end 502. In one or more embodiments, a portion of second transitory connector 100 may be disposed in assembled optic fiber fixture 500 wherein superior arm barb 123 is disposed in proximal barb interface 550 and inferior arm barb 133 is disposed in proximal barb interface 550. Illustratively, a portion of second transitory connector 100 may be disposed in assembled optic fiber fixture 500 wherein superior arm barb 123 is in contact with an outer perimeter of proximal barb interface 550 and wherein inferior arm barb 133 is in contact with the outer perimeter of proximal barb interface 550. In one or more embodiments, a portion of second transitory connector 100 may be disposed in assembled optic fiber fixture 500 wherein superior arm 120 and inferior arm 130 are disposed in proximal arm interface 555. Illustratively, a portion of second transitory connector 100 may be disposed in assembled optic fiber fixture 500 wherein superior arm 120 is in contact with an outer perimeter of proximal arm interface 555 and wherein inferior arm 130 is in contact with the outer perimeter of proximal arm interface 555. In one or more embodiments, transitory connector proximal housing proximal taper 545 may be configured to prevent superior arm barb 123 and inferior arm barb 133 from advancing into transitory connector proximal housing 540, e.g., a portion of superior arm barb 123 and a portion of inferior arm barb 133 may contact an outer perimeter of transitory connector proximal housing proximal taper 545.

Illustratively, inserting a portion of second transitory connector 100 into transitory connector proximal housing 540 may be configured to ingress optic fiber proximal end 212 into transitory connector proximal housing distal taper 535. In one or more embodiments, transitory connector proximal housing distal taper 535 may be configured to guide an ingress of optic fiber proximal end 212 into fixture base inner bore 530. Illustratively, fixture base inner bore 530 may be configured to guide an ingress of optic fiber proximal end 212 into machine connector proximal inner lumen 525. In one or more embodiments, inner lumen proximal taper 520 may be configured to guide an ingress of optic fiber proximal end 212 into machine connector distal inner lumen 515. Illustratively, inner lumen distal taper 510 may be configured to guide an ingress of optic fiber proximal end 212 into optic fiber proximal end guide 505. In one or more embodiments, a distance that optic fiber proximal end 212 extends from second transitory connector distal end 101 may be configured to cause optic fiber proximal end 212 to be adjacent to assembled optic fiber fixture proximal end 502 when second transitory connector 100 is inserted into transitory connector proximal housing 540.

Illustratively, a user may perform a photocoagulation procedure with assembled straight laser probe with replaceable optic fibers 1000. In one or more embodiments, a user may connect machine connector 440 to a laser machine. Illustratively, a user may energize the laser machine to deliver laser light into optic fiber proximal end 212, through optic fiber 210, out from optic fiber distal end 211, and onto a surgical target site. In one or more embodiments, assembled handle 900 may be a reusable medical device sold non-sterile and sterilized by a user in a medical autoclave. Illustratively, assembled replaceable fiber 300 may be a single-use medical device sold sterile and discarded after use.

Figure 11A:
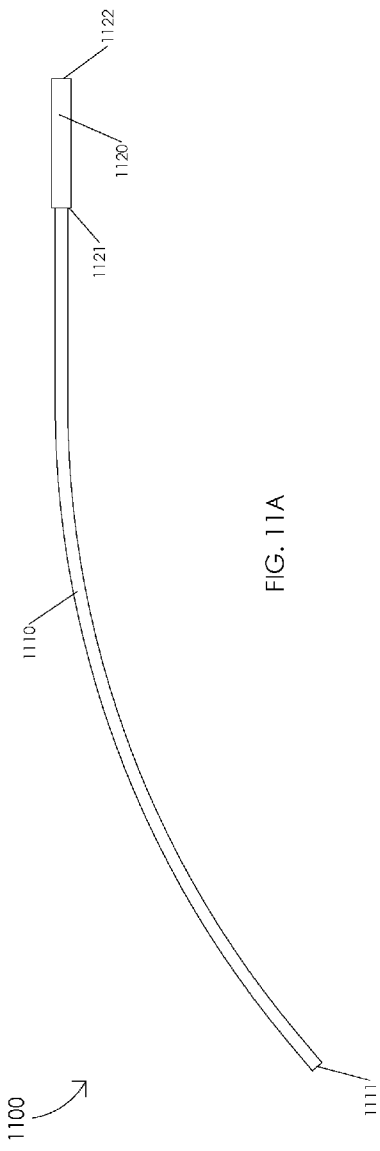
FIGS. 11A and 11B are schematic diagrams illustrating an assembled curved hypodermic tube.
Figure 11B:
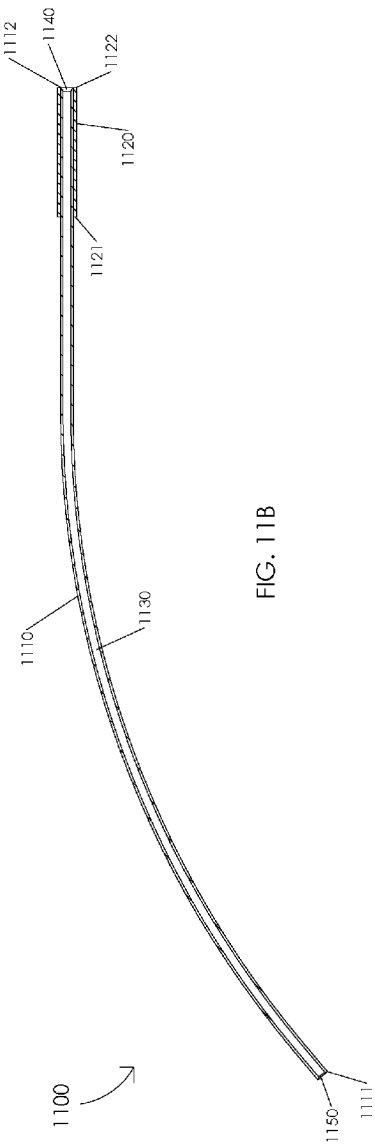

FIGS. 11A and 11B are schematic diagrams illustrating an assembled curved hypodermic tube 1100. FIG. 11A illustrates a side view of an assembled curved hypodermic tube 1100. FIG. 11B illustrates a cross-sectional view in a sagittal plane of an assembled curved hypodermic tube 1100. Illustratively, assembled curved hypodermic tube 1100 may comprise a curved tube 1110 and a bushing 1120. In one or more embodiments, curved tube 1110 may comprise a curved tube distal end 1111 and a curved tube proximal end 1112. Illustratively, curved tube 1110 may comprise a curved tube inner lumen 1130, a curved tube proximal taper 1140, and a curved tube distal taper 1150. In one or more embodiments, bushing 1120 may comprise a bushing distal end 1121 and a bushing proximal end 1122. Illustratively, a portion of curved tube 1110 may be disposed in bushing 1120, e.g., a portion of curved tube 1110 may be disposed in bushing 1120 wherein curved tube proximal end 1112 is adjacent to bushing proximal end 1122. In one or more embodiments, a portion of curved tube 1110 may be disposed in bushing 1120 wherein bushing distal end 1121 is disposed between curved tube distal end 1111 and curved tube proximal end 1122.

Figure 12A:
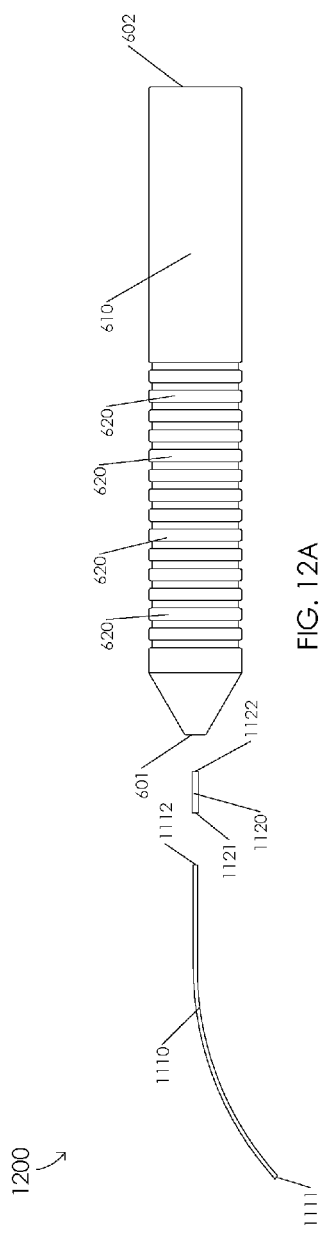
FIGS. 12A and 12B are schematic diagrams illustrating an exploded view of a curved laser probe handle assembly.
Figure 12B:
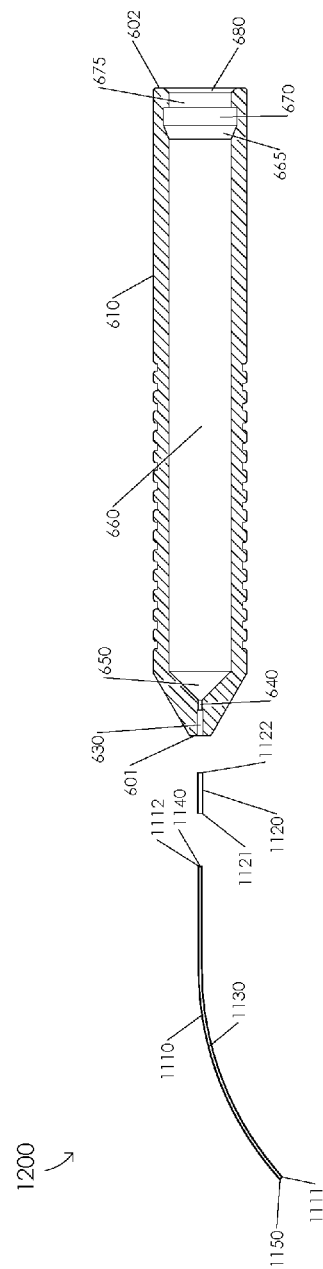
Figure 13A:
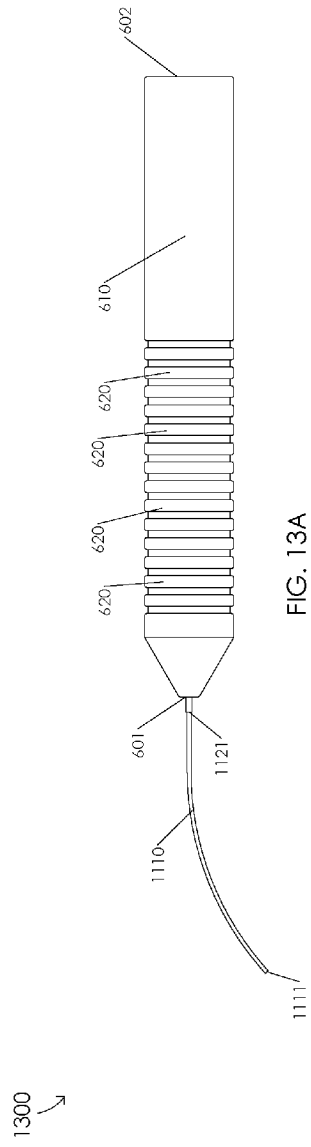
FIGS. 13A and 13B are schematic diagrams illustrating an assembled curved laser probe handle.
Figure 13B:
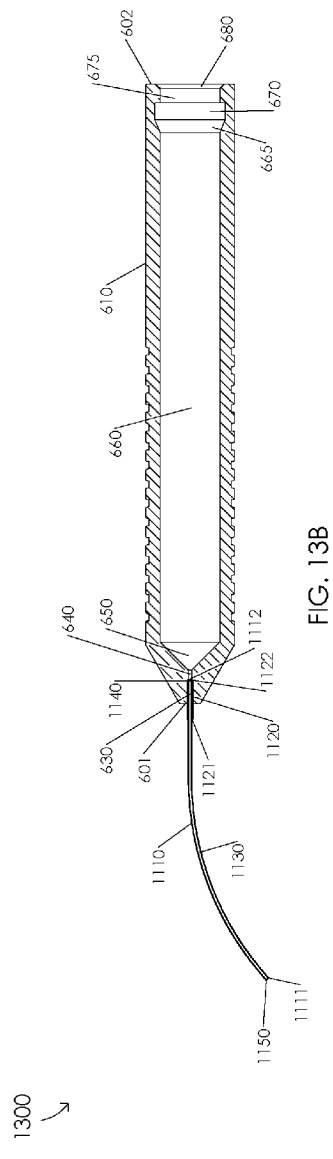

FIGS. 12A and 12B are schematic diagrams illustrating an exploded view of a curved laser probe handle assembly 1200. FIG. 12A illustrates a side view of a curved laser probe handle assembly 1200. FIG. 12B illustrates a cross-sectional view in a sagittal plane of a curved laser probe handle assembly 1200. Illustratively, curved laser probe handle assembly 1200 may comprise a curved tube 1110, a bushing 1120, and a handle base 600. FIGS. 13A and 13B are schematic diagrams illustrating an assembled curved laser probe handle 1300. FIG. 13A illustrates a side view of an assembled curved laser probe handle 1300. FIG. 13B illustrates a cross-sectional view in a sagittal plane of an assembled curved laser probe handle 1300. Illustratively, a portion of curved tube 1110 and a portion of bushing 1120 may be disposed in handle base 600, e.g., curved tube proximal end 1112 and bushing proximal end 1122 may be disposed in hypodermic tube housing 630. In one or more embodiments, curved tube proximal end 1112 and bushing proximal end 1122 may be fixed in hypodermic tube housing 630, e.g., curved tube proximal end 1112 and bushing proximal end 1122 may be fixed in hypodermic tube housing 630 by an adhesive, a crimp, a weld, a friction fit, etc.

Figure 14A:
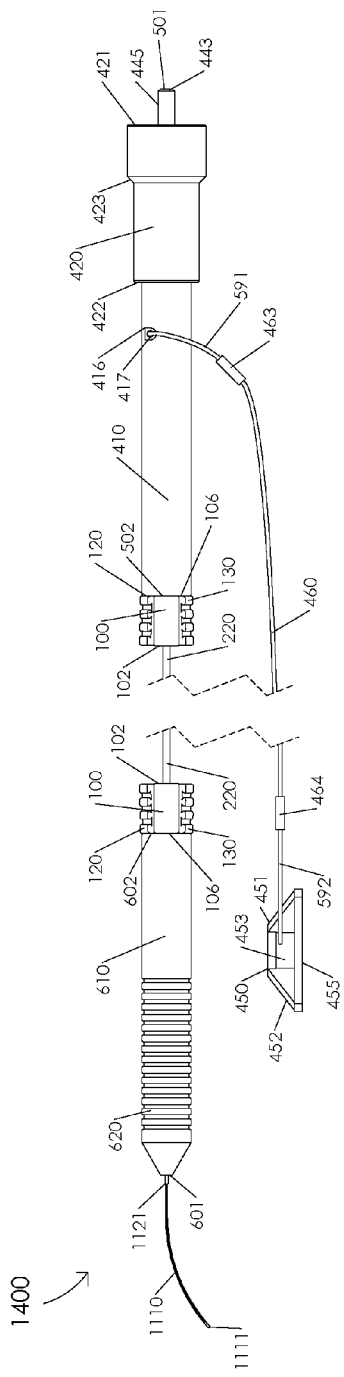
FIGS. 14A and 14B are schematic diagrams illustrating an assembled curved laser probe with replaceable fibers.
Figure 14B:
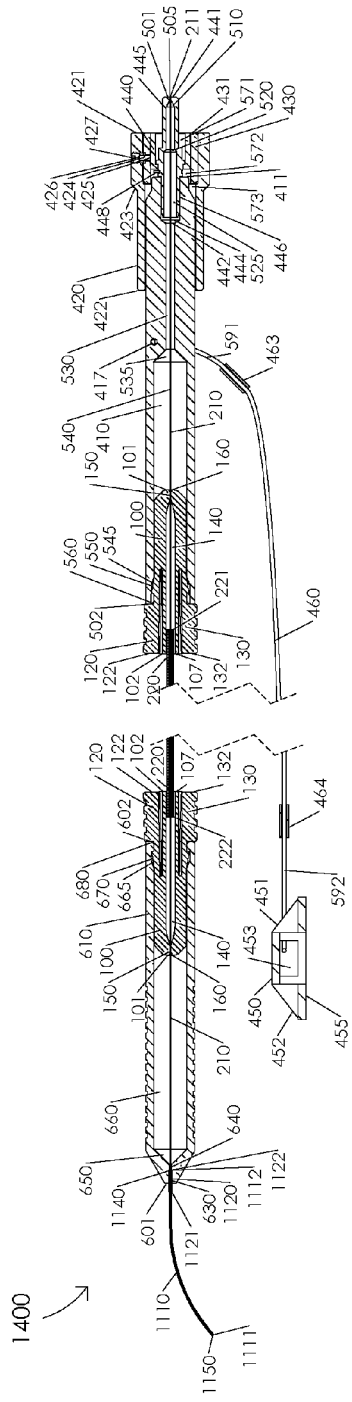

FIGS. 14A and 14B are schematic diagrams illustrating an assembled curved laser probe with replaceable fibers 1400. FIG. 14A illustrates a side view of an assembled curved laser probe with replaceable fibers 1400. FIG. 14B illustrates a cross-sectional view in a sagittal plane of an assembled curved laser probe with replaceable fibers 1400. Illustratively, an assembled curved laser probe with replaceable fibers 1400 may comprise an assembled replaceable fiber 300, an assembled curved laser probe handle 1300, and an assembled optic fiber fixture 500. In one or more embodiments, a portion of a first transitory connector 100 may be disposed in assembled curved laser probe handle 1300, e.g., first transitory connector distal end 101 may be disposed in transitory connector distal housing 660. Illustratively, a portion of first transitory connector 100 may extend a distance from handle base proximal end 602, e.g., first transitory connector proximal end 102 may extend a distance from handle base proximal end 602. In one or more embodiments, a portion of first transitory connector 100 may be disposed in assembled curved laser probe handle 1300 wherein superior arm barb 123 is disposed in distal barb interface 670 and inferior arm barb 133 is disposed in distal barb interface 670. Illustratively, a portion of first transitory connector 100 may be disposed in assembled curved laser probe handle 1300 wherein superior arm barb 123 is in contact with an outer perimeter of distal barb interface 670 and wherein inferior arm barb 133 is in contact with the outer perimeter of distal barb interface 670. In one or more embodiments, a portion of first transitory connector 100 may be disposed in assembled curved laser probe handle 1300 wherein superior arm 120 and inferior arm 130 are disposed in distal arm interface 675. Illustratively, a portion of first transitory connector 100 may be disposed in assembled curved laser probe handle 1300 wherein superior arm 120 is in contact with an outer perimeter of distal arm interface 675 and wherein inferior arm 130 is in contact with the outer perimeter of distal arm interface 675. In one or more embodiments, transitory connector distal housing proximal taper 665 may be configured to prevent superior arm barb 123 and inferior arm barb 133 from advancing into transitory connector distal housing 660, e.g., a portion of superior arm barb 123 and a portion of inferior arm barb 133 may contact an outer perimeter of transitory connector distal housing proximal taper 665. Illustratively, inserting a portion of first transitory connector 100 into transitory connector distal housing 660 may be configured to ingress optic fiber distal end 211 into transitory connector distal housing distal taper 650. In one or more embodiments, transitory connector distal housing distal taper 650 may be configured to guide an ingress of optic fiber distal end 211 into optic fiber guide 640. Illustratively, curved tube proximal taper 1140 may be configured to guide an ingress of optic fiber distal end 211 into curved tube inner lumen 1130. In one or more embodiments, a distance that optic fiber distal end 211 extends from first transitory connector distal end 101 may be configured to cause optic fiber distal end 211 to be adjacent to curved tube distal end 1111 when first transitory connector 100 is inserted into transitory connector distal housing 660.

Illustratively, curved tube distal taper 1150 may be configured to prevent degradation to a laser spot wherein optic fiber distal end 211 is recessed from curved tube distal end 1111 relative to a laser spot wherein optic fiber distal end 211 is coplanar with curved tube distal end 1111. In one or more embodiments, curved tube distal taper 1150 may be configured to ensure that a power output wherein optic fiber distal end 211 is recessed relative to curved tube distal end 1111 is identical to a power output wherein optic fiber distal end 211 is coplanar with curved tube distal end 1111. Illustratively, curved tube distal taper 1150 may be configured to ensure that a laser spot size wherein optic fiber distal end 211 is recessed relative to curved tube distal end 1111 is identical to a laser spot size wherein optic fiber distal end 211 is coplanar with curved tube distal end 1111. In one or more embodiments, curved tube distal taper 1150 may be configured to ensure that a laser spot shape wherein optic fiber distal end 211 is recessed relative to curved tube distal end 1111 is identical to a laser spot shape wherein optic fiber distal end 211 is coplanar with curved tube distal end 1111.

In one or more embodiments, a portion of a second transitory connector 100 may be disposed in assembled optic fiber fixture 500, e.g., second transitory connector distal end 101 may be disposed in transitory connector proximal housing 540. Illustratively, a portion of second transitory connector 100 may extend a distance from assembled optic fiber fixture proximal end 502, e.g., second transitory connector proximal end 102 may extend a distance from assembled optic fiber fixture proximal end 502. In one or more embodiments, a portion of second transitory connector 100 may be disposed in assembled optic fiber fixture 500 wherein superior arm barb 123 is disposed in proximal barb interface 550 and inferior arm barb 133 is disposed in proximal barb interface 550. Illustratively, a portion of second transitory connector 100 may be disposed in assembled optic fiber fixture 500 wherein superior arm barb 123 is in contact with an outer perimeter of proximal barb interface 550 and wherein inferior arm barb 133 is in contact with the outer perimeter of proximal barb interface 550. In one or more embodiments, a portion of second transitory connector 100 may be disposed in assembled optic fiber fixture 500 wherein superior arm 120 and inferior arm 130 are disposed in proximal arm interface 555. Illustratively, a portion of second transitory connector 100 may be disposed in assembled optic fiber fixture 500 wherein superior arm 120 is in contact with an outer perimeter of proximal arm interface 555 and wherein inferior arm 130 is in contact with the outer perimeter of proximal arm interface 555. In one or more embodiments, transitory connector proximal housing proximal taper 545 may be configured to prevent superior arm barb 123 and inferior arm barb 133 from advancing into transitory connector proximal housing 540, e.g., a portion of superior arm barb 123 and a portion of inferior arm barb 133 may contact an outer perimeter of transitory connector proximal housing proximal taper 545.

Illustratively, inserting a portion of second transitory connector 100 into transitory connector proximal housing 540 may be configured to ingress optic fiber proximal end 212 into transitory connector proximal housing distal taper 535. In one or more embodiments, transitory connector proximal housing distal taper 535 may be configured to guide an ingress of optic fiber proximal end 212 into fixture base inner bore 530. Illustratively, fixture base inner bore 530 may be configured to guide an ingress of optic fiber proximal end 212 into machine connector proximal inner lumen 525. In one or more embodiments, inner lumen proximal taper 520 may be configured to guide an ingress of optic fiber proximal end 212 into machine connector distal inner lumen 515. Illustratively, inner lumen distal taper 510 may be configured to guide an ingress of optic fiber proximal end 212 into optic fiber proximal end guide 505. In one or more embodiments, a distance that optic fiber proximal end 212 extends from second transitory connector distal end 101 may be configured to cause optic fiber proximal end 212 to be adjacent to assembled optic fiber fixture proximal end 502 when second transitory connector 100 is inserted into transitory connector proximal housing 540.

Illustratively, a user may perform a photocoagulation procedure with assembled curved laser probe with replaceable fibers 1400. In one or more embodiments, a user may connect machine connector 440 to a laser machine. Illustratively, a user may energize the laser machine to deliver laser light into optic fiber proximal end 212, through optic fiber 210, out from optic fiber distal end 211, and onto a surgical target site. In one or more embodiments, assembled curved laser probe handle 1300 may be a reusable medical device sold non-sterile and sterilized by a user in a medical autoclave. Illustratively, assembled replaceable fiber 300 may be a single-use medical device sold sterile and discarded after use.

FIGS. 15A and 15B are schematic diagrams illustrating an assembled steerable hypodermic tube 1500. FIG. 15A illustrates a side view of an assembled steerable hypodermic tube 1500. FIG. 15B illustrates a cross-sectional view in a sagittal plane of an assembled steerable hypodermic tube 1500. Illustratively, assembled steerable hypodermic tube 1500 may comprise a steerable hypodermic tube 1510 and a wire 1520. In one or more embodiments, steerable hypodermic tube 1510 may comprise a steerable hypodermic tube distal end 1511 and a steerable hypodermic tube proximal end 1512. Illustratively, steerable hypodermic tube 1510 may comprise a steerable hypodermic tube inner lumen 1530 and a flexible portion 1515. In one or more embodiments, flexible portion 1515 may comprise a plurality of apertures 1513. Illustratively, wire 1520 may comprise a wire distal end 1521 and a wire proximal end 1522. In one or more embodiments, a portion of wire 1520 may be disposed in steerable hypodermic tube inner lumen 1530, e.g., wire distal end 1521 may be disposed in steerable hypodermic tube inner lumen 1530. Illustratively, a portion of wire 1520 may be fixed in steerable hypodermic tube inner lumen 1530, e.g. a portion of wire 1520 may be fixed in steerable hypodermic tube inner lumen 1530 by an adhesive, a crimp, a tie, a weld, etc.

Figure 16:
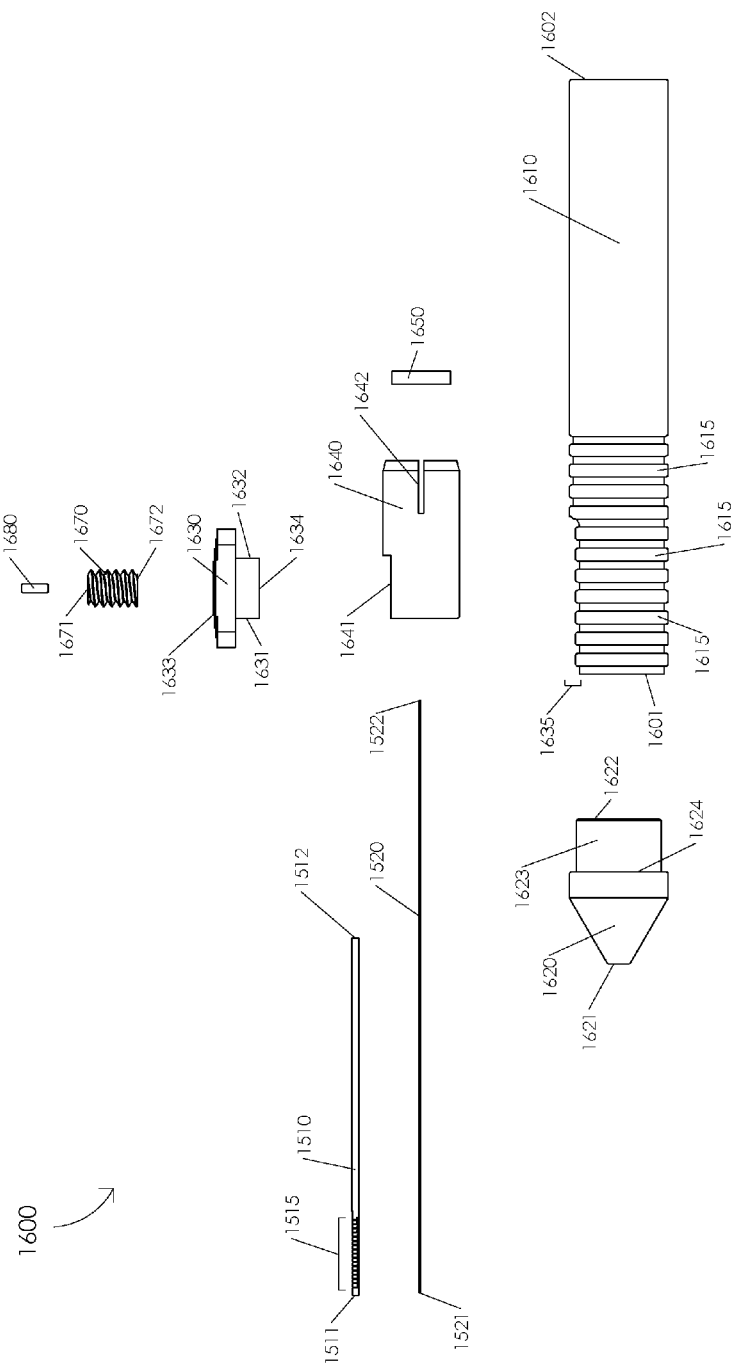
FIG. 16 is a schematic diagram illustrating an exploded view of a steerable handle assembly.

FIG. 16 is a schematic diagram illustrating an exploded view of a steerable handle assembly 1600. Illustratively, a steerable handle assembly 1600 may comprise a steerable hypodermic tube 1510, a wire 1520, a steerable handle base 1610, a nosecone 1620, a slider 1630, a piston 1640, an expansion ring 1650, a setscrew, and a pin 1680. In one or more embodiments, steerable handle base 1610 may comprise a steerable handle base distal end 1601 and a steerable base handle proximal end 1602. Illustratively, steerable handle base 1610 may comprise a plurality of grip points 1615. In one or more embodiments, steerable handle base 1610 may comprise a slider guide 1635. Illustratively, nosecone 1620 may comprise a nosecone distal end 1621 and a nosecone proximal end 1622. In one or more embodiments, nosecone 1620 may comprise a nosecone base 1623 and a nosecone lip 1624. Illustratively, slider 1630 may comprise a slider distal end 1631, a slider proximal end 1632, a slider superior end 1633, and a slider inferior end 1634. In one or more embodiments, piston 1640 may comprise a slider housing 1641 and a slot 1642. Illustratively, piston 1640 may comprise a plurality of slots 1642 disposed around an outer perimeter of piston 1640. In one or more embodiments, each slot 1642 of a plurality of slots 1642 may be disposed between solid portions of piston 1640. In one or more embodiments, expansion ring 1650 may be disposed in a portion of piston 1640, e.g., expansion ring 1650 may be fixed in a portion of piston 1640. Illustratively, expansion ring 1650 may be configured to radially expand one or more solid portions of piston 1640 separated by slot 1642. In one or more embodiments, setscrew 1670 may comprise a setscrew superior end 1671 and a setscrew inferior end 1672.

Figure 17C:
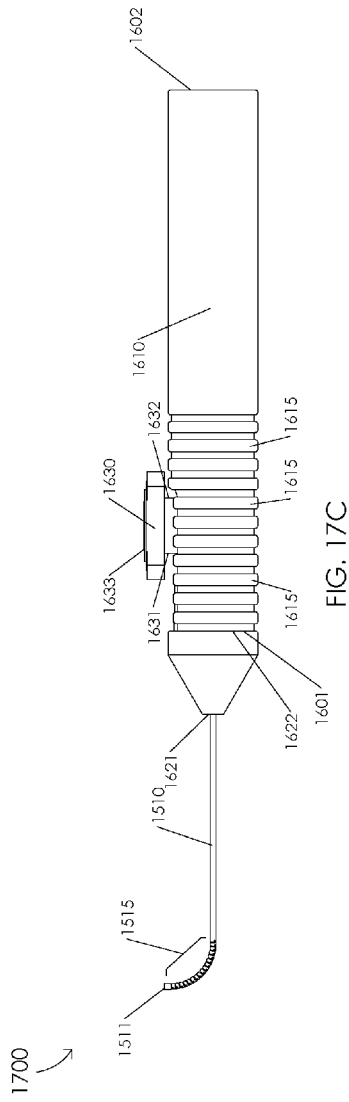

FIGS. 17A, 17B, 17C, and 17D are schematic diagrams illustrating an assembled steerable handle 1700. FIG. 17A illustrates a side view of an assembled steerable handle 1700 with a straight steerable hypodermic tube 1510. FIG. 17B illustrates a cross-sectional view in a sagittal plane of an assembled steerable handle 1700 with a straight steerable hypodermic tube 1510. Illustratively, an assembled steerable handle 1700 may comprise a transitory connector distal housing 1702, a transitory connector distal housing distal taper 1702, a transitory connector distal housing proximal taper 1703, and a steerable guide 1704. In one or more embodiments, assembled steerable handle 1700 may comprise a distal barb interface 1705, a distal arm interface 1706, and a steerable handle base inner taper 1707. Illustratively, assembled steerable handle 1700 may comprise a piston guide distal taper 1710, a piston guide 1720, a piston taper 1722, a steerable hypodermic tube housing 1723, an optic fiber guide 1724, and a piston inner lumen 1730.

In one or more embodiments, piston 1640 may be disposed in piston guide 1720, e.g., piston 1640 may be disposed in piston guide 1720 wherein piston 1640 may actuate within piston guide 1720. Illustratively, expansion ring 1650 may be disposed in piston 1640 wherein expansion ring 1650 radially expands a plurality of solid portion of piston 1640 separated by slot 1642. In one or more embodiments, expanding the plurality of solid portions of piston 1640 separated by slot 1642 may be configured to create a force of friction between the plurality of solid portions of piston 1640 and an outer perimeter of piston guide 1720. Illustratively, the force of friction between the plurality of solid portions of piston 1640 and the outer perimeter of piston guide 1720 may be configured to prevent piston 1640 from actuating within piston guide 1720.

In one or more embodiments, a portion of nosecone 1620 may be disposed in steerable handle base 1610, e.g., nosecone proximal end 1622 may be disposed in steerable handle base 1610. Illustratively, nosecone 1620 may be fixed in steerable handle base 1610, e.g., nosecone 1620 may be fixed in steerable handle base 1610 by a friction fit, an adhesive, a setscrew, a weld, etc. In one or more embodiments, a portion of steerable hypodermic tube 1510 may be disposed in nosecone 1620, e.g., steerable hypodermic tube proximal end 1512 may be disposed in steerable hypodermic tube housing 1723. Illustratively, steerable hypodermic tube proximal end 1512 may be fixed in steerable hypodermic tube housing 1723, e.g., steerable hypodermic tube proximal end 1512 may be fixed in steerable hypodermic tube housing 1723 by a friction fit, an adhesive, a setscrew, a weld, etc.

In one or more embodiments, slider 1630 may be disposed in slider guide 1635 and piston 1640, e.g., slider inferior end 1634 may be disposed in slider guide 1635 and piston 1640. Illustratively, slider 1630 may be configured to actuate within slider guide 1635. In one or more embodiments, slider 1630 may be fixed in piston 1640, e.g., slider 1630 may be fixed in piston 1640 by an adhesive, a friction fit, a setscrew, etc. Illustratively, setscrew 1670 may be configured to fix slider 1630 in piston 1640. In one or more embodiments, setscrew 1670 may be disposed in slider 1630 and piston 1640. Illustratively, setscrew 1670 may be fixed in slider 1630 and piston 1640. In one or more embodiments, pin 1680 may be disposed in setscrew 1670, e.g., pin 1680 may be fixed in setscrew 1670 by a friction fit, an adhesive, a weld, etc. Illustratively, wire 1520 may be disposed in steerable hypodermic tube inner lumen 1530, optic fiber guide 1724, piston guide 1720, piston inner lumen 1730, and setscrew 1670. In one or more embodiments, wire 1520 may be fixed in steerable hypodermic tube inner lumen 1530 and wire 1520 may be fixed in setscrew 1670, e.g., pin 1680 may be configured to fix wire 1520 in setscrew 1670.

Figure 17D:
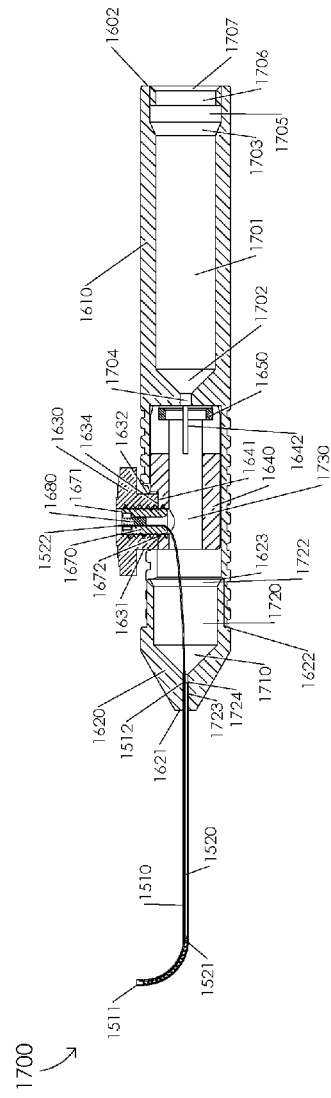

FIG. 17C illustrates a side view of an assembled steerable handle 1700 with a curved steerable hypodermic tube 1510. FIG. 17D illustrates a cross-sectional view in a sagittal plane of an assembled steerable handle 1700 with a curved steerable hypodermic tube 1510. Illustratively, applying a force to a portion of slider 1630 may be configured to actuate slider 1630 within slider guide 1635, e.g., applying a force to a portion of slider 1630 greater than a force of friction between a plurality of solid portions of piston 1640 and an outer perimeter of piston guide 1720 may be configured to actuate slider 1630 within slider guide 1635. In one or more embodiments, applying a force to a portion of slider 1630 may be configured to actuate piston 1640 within piston guide 1720, e.g., applying a force to a portion of slider 1630 greater than a force of friction between a plurality of solid portions of piston 1640 and an outer perimeter of piston guide 1720 may be configured to actuate piston 1640 within piston guide 1720.

Illustratively, a retraction of slider 1630 away from nosecone distal end 1621 may be configured to retract piston 1640 away from nosecone distal end 1621. In one or more embodiments, a retraction of piston 1640 relative to nosecone distal end 1621 may be configured to retract wire 1520 relative to steerable hypodermic tube 1510. Illustratively, a retraction of wire 1520 relative to steerable hypodermic tube 1510 may be configured to apply a force to a portion of steerable hypodermic tube 1510. In one or more embodiments, an application of a force to a portion of steerable hypodermic tube 1510 may be configured to collapse one or more apertures 1513 of a plurality of apertures 1513. Illustratively, a collapse of one or more apertures 1513 of a plurality of apertures 1513 may be configured to curve steerable hypodermic tube 1510. In one or more embodiments, removing an applied force from a portion of slider 1630 may be configured to temporarily fix steerable hypodermic tube 1510 in a curved position, e.g., a force of friction between a plurality of solid portions of piston 1640 and an outer perimeter of piston guide 1720 may be configured to temporarily fix steerable hypodermic tube 1510 in a curved position.

Illustratively, an extension of slider 1630 towards nosecone distal end 1621 may be configured to extend piston 1640 towards nosecone distal end 1621. In one or more embodiments, an extension of piston 1640 relative to nosecone distal end 1621 may be configured to extend wire 1520 relative to steerable hypodermic tube 1510. Illustratively, an extension of wire 1520 relative to steerable hypodermic tube 1510 may be configured to reduce a force applied to a portion of steerable hypodermic tube 1510. In one or more embodiments, a reduction of a force applied to a portion of steerable hypodermic tube 1510 may be configured to expand one or more apertures 1513 of a plurality of apertures 1513. Illustratively, an expansion of one or more apertures 1513 of a plurality of apertures 1513 may be configured to straighten steerable hypodermic tube 1510. In one or more embodiments, removing an applied force from a portion of slider 1630 may be configured to temporarily fix steerable hypodermic tube 1510 in a straight position, e.g., a force of friction between a plurality of solid portions of piston 1640 and an outer perimeter of piston guide 1720 may be configured to temporarily fix steerable hypodermic tube 1510 in a straight position.

FIGS. 18A and 18B are schematic diagrams illustrating an assembled steerable laser probe with replaceable fibers 1800. FIG. 18A illustrates a side view of an assembled steerable laser probe with replaceable fibers 1800. FIG. 18B illustrates a cross-sectional view in a sagittal plane of an assembled steerable laser probe with replaceable fibers 1800. Illustratively, an assembled steerable laser probe with replaceable fibers 1800 may comprise an assembled replaceable fiber 300, an assembled steerable handle 1700, and an assembled optic fiber fixture 500. In one or more embodiments, a portion of a first transitory connector 100 may be disposed in assembled steerable handle 1700, e.g., first transitory connector distal end 101 may be disposed in transitory connector distal housing 1701. Illustratively, a portion of first transitory connector 100 may extend a distance from steerable handle base proximal end 1602, e.g., first transitory connector proximal end 102 may extend a distance from steerable handle base proximal end 1602. In one or more embodiments, a portion of first transitory connector 100 may be disposed in assembled steerable handle 1700 wherein superior arm barb 123 is disposed in distal barb interface 1705 and inferior arm barb 133 is disposed in distal barb interface 1705. Illustratively, a portion of first transitory connector 100 may be disposed in assembled steerable handle 1700 wherein superior arm barb 123 is in contact with an outer perimeter of distal barb interface 1705 and wherein inferior arm barb 133 is in contact with the outer perimeter of distal barb interface 1705. In one or more embodiments, a portion of first transitory connector 100 may be disposed in assembled steerable handle 1700 wherein superior arm 120 and inferior arm 130 are disposed in distal arm interface 1706. Illustratively, a portion of first transitory connector 100 may be disposed in assembled steerable handle 1700 wherein superior arm 120 is in contact with an outer perimeter of distal arm interface 1706 and wherein inferior arm 130 is in contact with the outer perimeter of distal arm interface 1706. In one or more embodiments, transitory connector distal housing proximal taper 1703 may be configured to prevent superior arm barb 123 and inferior arm barb 133 from advancing into transitory connector distal housing 1701, e.g., a portion of superior arm barb 123 and a portion of inferior arm barb 133 may contact an outer perimeter of transitory connector distal housing proximal taper 1703.

Illustratively, inserting a portion of first transitory connector 100 into transitory connector distal housing 1701 may be configured to ingress optic fiber distal end 211 into transitory connector distal housing distal taper 1701. In one or more embodiments, transitory connector distal housing distal taper 1702 may be configured to guide an ingress of optic fiber distal end 211 into steerable guide 1704. Illustratively, steerable guide 1704 may be configured to guide an ingress of optic fiber distal end 211 into piston inner lumen 1730. In one or more embodiments, piston taper 1722 may be configured to guide an ingress of optic fiber distal end 211 into piston guide 1720. Illustratively, piston guide distal taper 1710 may be configured to guide an ingress of optic fiber distal end 211 into optic fiber guide 1724. In one or more embodiments, optic fiber guide 1724 may be configured to guide an ingress of optic fiber distal end 211 into steerable hypodermic tube inner lumen 1530. Illustratively, a distance that optic fiber distal end 211 extends from first transitory connector distal end 101 may be configured to cause optic fiber distal end 211 to be adjacent to steerable hypodermic tube distal end 1511 when first transitory connector 100 is inserted into transitory connector distal housing 1701. Illustratively, steerable hypodermic 1510 may comprise a distal taper configured to prevent degradation to a laser spot wherein optic fiber distal end 211 is recessed from steerable hypodermic tube distal end 1511 relative to a laser spot wherein optic fiber distal end 211 is coplanar with steerable hypodermic tube distal end 1511. In one or more embodiments, steerable hypodermic 1510 may comprise a distal taper configured to ensure that a power output wherein optic fiber distal end 211 is recessed relative to steerable hypodermic tube distal end 1511 is identical to a power output wherein optic fiber distal end 211 is coplanar with steerable hypodermic tube distal end 1511. Illustratively, steerable hypodermic 1510 may comprise a distal taper configured to ensure that a laser spot size wherein optic fiber distal end 211 is recessed relative to steerable hypodermic tube distal end 1511 is identical to a laser spot size wherein optic fiber distal end 211 is coplanar with steerable hypodermic tube distal end 1511. In one or more embodiments, steerable hypodermic 1510 may comprise a distal taper configured to ensure that a laser spot shape wherein optic fiber distal end 211 is recessed relative to curved tube distal end 1111 is identical to a laser spot shape wherein optic fiber distal end 211 is coplanar with curved tube distal end 1111.

In one or more embodiments, a portion of a second transitory connector 100 may be disposed in assembled optic fiber fixture 500, e.g., second transitory connector distal end 101 may be disposed in transitory connector proximal housing 540. Illustratively, a portion of second transitory connector 100 may extend a distance from assembled optic fiber fixture proximal end 502, e.g., second transitory connector proximal end 102 may extend a distance from assembled optic fiber fixture proximal end 502. In one or more embodiments, a portion of second transitory connector 100 may be disposed in assembled optic fiber fixture 500 wherein superior arm barb 123 is disposed in proximal barb interface 550 and inferior arm barb 133 is disposed in proximal barb interface 550. Illustratively, a portion of second transitory connector 100 may be disposed in assembled optic fiber fixture 500 wherein superior arm barb 123 is in contact with an outer perimeter of proximal barb interface 550 and wherein inferior arm barb 133 is in contact with the outer perimeter of proximal barb interface 550. In one or more embodiments, a portion of second transitory connector 100 may be disposed in assembled optic fiber fixture 500 wherein superior arm 120 and inferior arm 130 are disposed in proximal arm interface 555. Illustratively, a portion of second transitory connector 100 may be disposed in assembled optic fiber fixture 500 wherein superior arm 120 is in contact with an outer perimeter of proximal arm interface 555 and wherein inferior arm 130 is in contact with the outer perimeter of proximal arm interface 555. In one or more embodiments, transitory connector proximal housing proximal taper 545 may be configured to prevent superior arm barb 123 and inferior arm barb 133 from advancing into transitory connector proximal housing 540, e.g., a portion of superior arm barb 123 and a portion of inferior arm barb 133 may contact an outer perimeter of transitory connector proximal housing proximal taper 545.

Illustratively, inserting a portion of second transitory connector 100 into transitory connector proximal housing 540 may be configured to ingress optic fiber proximal end 212 into transitory connector proximal housing distal taper 535. In one or more embodiments, transitory connector proximal housing distal taper 535 may be configured to guide an ingress of optic fiber proximal end 212 into fixture base inner bore 530. Illustratively, fixture base inner bore 530 may be configured to guide an ingress of optic fiber proximal end 212 into machine connector proximal inner lumen 525. In one or more embodiments, inner lumen proximal taper 520 may be configured to guide an ingress of optic fiber proximal end 212 into machine connector distal inner lumen 515. Illustratively, inner lumen distal taper 510 may be configured to guide an ingress of optic fiber proximal end 212 into optic fiber proximal end guide 505. In one or more embodiments, a distance that optic fiber proximal end 212 extends from second transitory connector distal end 101 may be configured to cause optic fiber proximal end 212 to be adjacent to assembled optic fiber fixture proximal end 502 when second transitory connector 100 is inserted into transitory connector proximal housing 540.

Illustratively, a user may perform a photocoagulation procedure with assembled steerable laser probe with replaceable fibers 1800. In one or more embodiments, a user may connect machine connector 440 to a laser machine. Illustratively, a user may energize the laser machine to deliver laser light into optic fiber proximal end 212, through optic fiber 210, out from optic fiber distal end 211, and onto a surgical target site. In one or more embodiments, assembled steerable handle 1700 may be a reusable medical device sold non-sterile and sterilized by a user in a medical autoclave. Illustratively, assembled replaceable fiber 300 may be a single-use medical device sold sterile and discarded after use.

Figure 19:
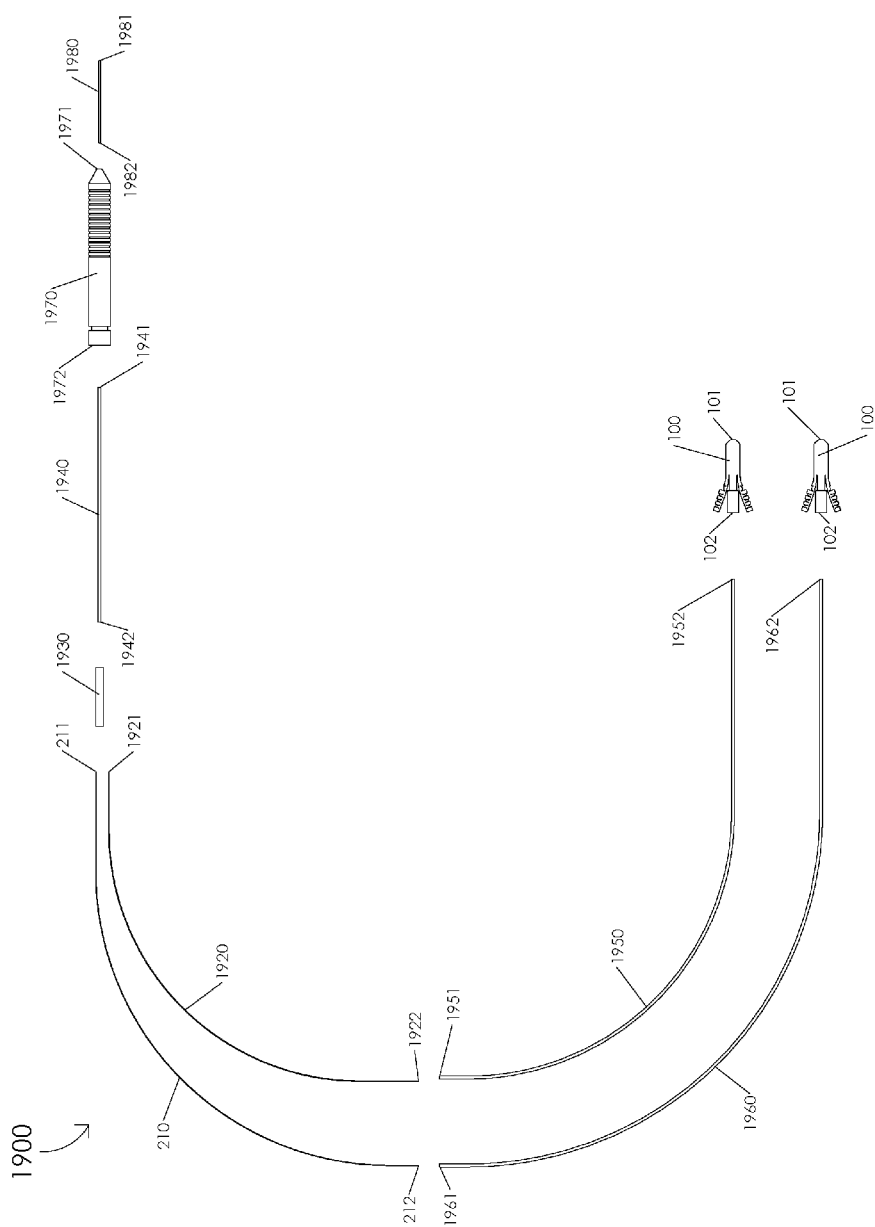
FIG. 19 is a schematic diagram illustrating an exploded view of a replaceable illuminated fiber assembly.

FIG. 19 is a schematic diagram illustrating an exploded view of a replaceable illuminated fiber assembly 1900. Illustratively, a replaceable illuminated fiber assembly 1900 may comprise a first transitory connector 100, a second transitory connector 100, an optic fiber 210, an illumination optic fiber 1920, a coupling sleeve 1930, a dual fiber housing 1940, an illumination jacketing 1950, a jacketing 1960, an illumination handle base 1970, and an illumination hypodermic tube 1980. In one or more embodiments, illumination optic fiber 1920 may comprise an illumination optic fiber distal end 1921 and an illumination optic fiber proximal end 1922. Illustratively, dual fiber housing 1940 may comprise a dual fiber housing distal end 1941 and a dual fiber housing proximal end 1942. In one or more embodiments, illumination jacketing 1950 may comprise an illumination jacketing distal end 1951 and an illumination jacketing proximal end 1952. Illustratively, jacketing 1960 may comprise a jacketing distal end 1961 and a jacketing proximal end 1962. In one or more embodiments, illumination handle base 1970 may comprise an illumination handle base distal end 1971 and an illumination handle base proximal end 1972. Illustratively, illumination hypodermic tube 1980 may comprise an illumination hypodermic tube distal end 1981 and an illumination hypodermic tube proximal end 1982.

FIGS. 20A and 20B are schematic diagrams illustrating an assembled illuminated handle 2000. FIG. 20A illustrates a side view of an assembled illuminated handle 2000. FIG. 20B illustrates a cross-sectional view in a sagittal plane of an assembled illuminated handle 2000. Illustratively, an assembled illuminated handle 2000 may comprise an illumination handle base inner lumen 2010 and an illumination handle base inner lumen distal taper 2020. In one or more embodiments, optic fiber proximal end 212 may extend a distance from first transitory connector distal end 101. Illustratively, illumination fiber proximal end 1922 may extend a distance from second transitory connector distal end 101. In one or more embodiments, optic fiber 210 may be disposed in jacketing 1960 wherein optic fiber distal end 211 extends a distance from jacketing distal end 1961 and wherein optic fiber proximal end 212 extends a distance from jacketing distal end 1962. Illustratively, illumination optic fiber 1920 may be disposed in illumination jacketing 1950 wherein illumination optic fiber distal end 1921 extends a distance from illumination jacketing distal end 1951 and wherein illumination optic fiber proximal end 1922 extends a distance from illumination jacketing proximal end 1952.

In one or more embodiments, a portion of illumination hypodermic tube 1980 may be disposed in illumination handle base 1970, e.g., illumination hypodermic tube proximal end 1982 may be disposed in illumination handle base 1970. Illustratively, illumination hypodermic tube proximal end 1982 may be fixed in illumination handle base 1970, e.g., illumination hypodermic tube proximal end 1982 may be fixed in illumination handle base 1970 by a friction fit, an adhesive, a weld, a setscrew, etc. In one or more embodiments, a portion of illumination jacketing 1950 may be disposed in coupling sleeve 1930, e.g., illumination jacketing distal end 1951 may be disposed in coupling sleeve 1930. Illustratively, illumination jacketing distal end 1951 may be fixed in coupling sleeve 1930. In one or more embodiments, a portion of jacketing 1960 may be disposed in coupling sleeve 1930, e.g., jacketing distal end 1961 may be disposed in coupling sleeve 1930. Illustratively, jacketing distal end 1961 may be fixed in coupling sleeve 1930. In one or more embodiments, a portion of dual fiber housing 1940 may be disposed in coupling sleeve 1930, e.g., dual fiber housing proximal end 1942 may be disposed in coupling sleeve 1930. Illustratively, dual fiber housing proximal end 1942 may be fixed in coupling sleeve 1930. In one or more embodiments, a portion of dual fiber housing 1940 may be disposed in illumination handle base 1970, e.g., dual fiber housing distal end 1941 may be disposed in illumination handle base inner lumen 2010. Illustratively, dual fiber housing distal end 1941 may be fixed in illumination handle base inner lumen 2010, e.g., dual fiber housing distal end 1941 may be fixed in illumination handle base inner lumen 2010 by a friction fit, an adhesive, a weld, a setscrew, etc.

In one or more embodiments, optic fiber 210 may be disposed in coupling sleeve 1930, dual fiber housing 1940, illumination handle base inner lumen 2010, illumination handle base inner lumen distal taper 2020, and illumination hypodermic tube 1980. Illustratively, optic fiber 210 may be disposed in illumination hypodermic tube 1980 wherein optic fiber distal end 211 is adjacent to illumination hypodermic tube distal end 1981, e.g., optic fiber 210 may be disposed in illumination hypodermic tube 1980 wherein optic fiber distal end 211 is coplanar with illumination hypodermic tube distal end 1981. In one or more embodiments, optic fiber 210 may be fixed in hypodermic tube 1980, e.g., optic fiber 210 may be fixed in hypodermic tube 1980 by an adhesive, an epoxy, or any suitable fixation means. Illustratively, illumination optic fiber 1920 may be disposed in coupling sleeve 1930, dual fiber housing 1940, illumination handle base inner lumen 2010, illumination handle base inner lumen distal taper 2020, and illumination hypodermic tube 1980. In one or more embodiments, illumination optic fiber 1920 may be disposed in illumination hypodermic tube 1980 wherein illumination optic fiber distal end 1921 is adjacent to illumination hypodermic tube distal end 1981, e.g., illumination optic fiber 1920 may be disposed in illumination hypodermic tube 1980 wherein illumination optic fiber distal end 1920 is coplanar with illumination hypodermic tube distal end 1981. Illustratively, illumination optic fiber 1920 may be fixed in hypodermic tube 1980, e.g., illumination optic fiber 1920 may be fixed in hypodermic tube 1980 by an adhesive, an epoxy, or any suitable fixation means.

In one or more embodiments, a portion of jacketing 1960 may be disposed in a portion of first transitory connector 100, e.g., jacketing proximal end 1962 may be disposed in tapered inner lumen 140. Illustratively, a portion of jacketing 1960 may be fixed in a portion of first transitory connector 100, e.g., a portion of jacketing 1960 may be fixed in a portion of first transitory connector 100 by an adhesive, a friction fit, a crimp, a tie, a weld, etc. In one or more embodiments, a portion of illumination jacketing 1950 may be disposed in a portion of second transitory connector 100, e.g., illumination jacketing proximal end 1952 may be disposed in tapered inner lumen 140. Illustratively, a portion of illumination jacketing 1950 may be fixed in a portion of second transitory connector 100, e.g., a portion of illumination jacketing 1950 may be fixed in a portion of second transitory connector 100 by an adhesive, a friction fit, a crimp, a tie, a weld, etc.

In one or more embodiments, optic fiber 210 may be disposed in first transitory connector 100 wherein optic fiber 210 is disposed in tapered inner lumen 140, optic fiber housing 150, and fixation mechanism housing 160. Illustratively, a portion of optic fiber 210 may be fixed within fixation mechanism housing 160, e.g., a portion of optic fiber 210 may be fixed within fixation mechanism housing 160 by an adhesive, a friction fit, a crimp, a tie, a weld, etc. In one or more embodiments, optic fiber 210 may be fixed in first transitory connector 100 wherein optic fiber proximal end 212 extends a fixed distance from first transitory connector distal end 101. Illustratively, illumination optic fiber 1920 may be disposed in second transitory connector 100 wherein illumination optic fiber 1920 is disposed in tapered inner lumen 140, optic fiber housing 150, and fixation mechanism housing 160. Illustratively, a portion of illumination optic fiber 1920 may be fixed within fixation mechanism housing 160, e.g., a portion of illumination optic fiber 1920 may be fixed within fixation mechanism housing 160 by an adhesive, a friction fit, a crimp, a tie, a weld, etc. In one or more embodiments, illumination optic fiber 1920 may be fixed in second transitory connector 100 wherein illumination optic fiber proximal end 1922 extends a fixed distance from second transitory connector distal end 101. Illustratively, a distance that optic fiber proximal end 212 extends from first transitory connector distal end 101 may be different from a distance that illumination optic fiber proximal end 1922 extends from second transitory connector distal end 101. In one or more embodiments, a distance that optic fiber proximal end 212 extends from first transitory connector distal end 101 and a distance that illumination optic fiber proximal end 1922 extends from second transitory connector distal end 101 may be configured to prevent a user from inserting optic fiber 210 into an illumination machine and to prevent a user from inserting illumination optic fiber 1920 into a laser machine.

Figure 21A:
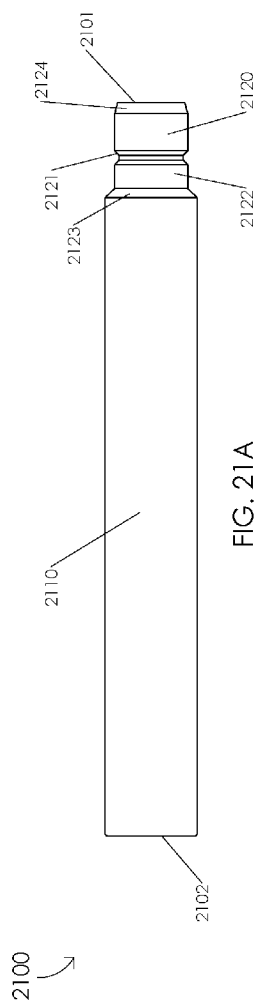
FIGS. 21A and 21B are schematic diagrams illustrating an illumination optic fiber fixture.
Figure 21B:
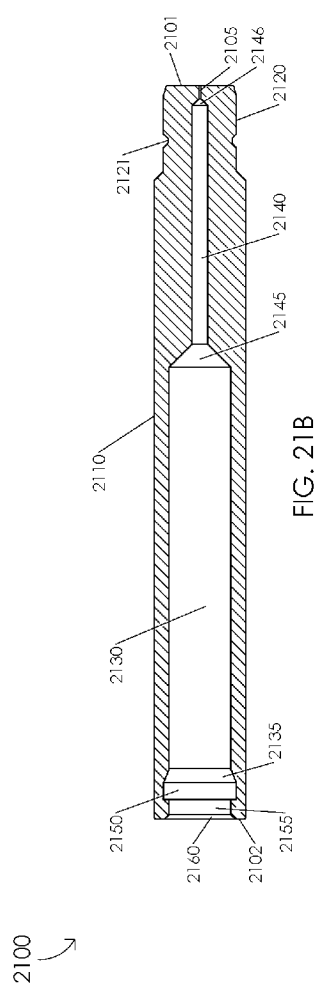

FIGS. 21A and 21B are schematic diagrams illustrating an illumination optic fiber fixture 2100. FIG. 21A illustrates a side view of an illumination optic fiber fixture 2100. Illustratively, an illumination optic fiber fixture 2100 may comprise an illumination optic fiber fixture distal end 2101 and an illumination optic fiber fixture proximal end 2102. In one or more embodiments, an illumination optic fiber fixture 2100 may comprise an illumination fixture base 2110, an illumination machine connector 2120, a channel 2121, an illumination machine connector base 2122, an illumination machine connector proximal taper 2123, and an illumination machine connector distal taper 2124. FIG. 21B illustrates a cross-sectional view in a sagittal plane of an illumination optic fiber fixture 2100. Illustratively, illumination optic fiber fixture 2100 may comprise an illumination optic fiber guide 2105, a transitory connector proximal housing 2130, a transitory connector proximal housing proximal taper 2135, an illumination optic fiber fixture inner bore 2140, a transitory connector proximal housing distal taper 2145, an illumination optic fiber fixture inner bore distal taper 2146, a proximal barb interface 2150, a proximal arm interface 2155, and an illumination optic fiber fixture inner taper 2160.

Figure 22A:
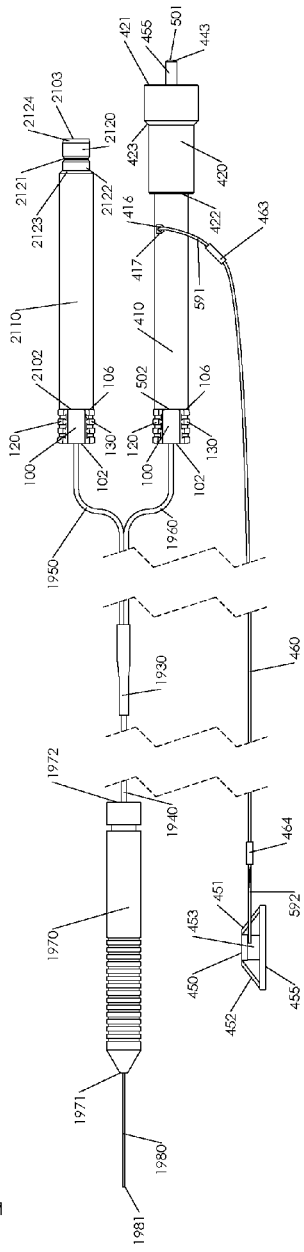
FIGS. 22A and 22B are schematic diagrams illustrating an assembled illuminated laser probe with replaceable fibers.
Figure 22B:
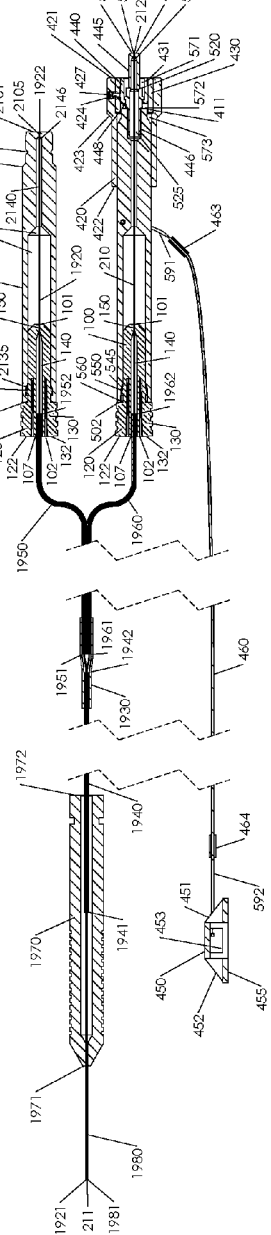

FIGS. 22A and 22B are schematic diagrams illustrating an assembled illuminated laser probe with replaceable fibers 2200. FIG. 22A illustrates a side view of an assembled illuminated laser probe with replaceable fibers 2200. FIG. 22B illustrates a cross-sectional view in a sagittal plane of an assembled illuminated laser probe with replaceable fibers 2200. Illustratively, an assembled illuminated laser probe with replaceable fibers 2200 may comprise an assembled illuminated handle 2000, an illumination optic fiber fixture 2100, and an assembled optic fiber fixture 500. In one or more embodiments, a portion of a first transitory connector 100 may be disposed in assembled optic fiber fixture 500, e.g., first transitory connector distal end 101 may be disposed in transitory connector proximal housing 540. Illustratively, a portion of first transitory connector 100 may extend a distance from assembled optic fiber fixture proximal end 502, e.g., first transitory connector proximal end 102 may extend a distance from assembled optic fiber fixture proximal end 502. In one or more embodiments, a portion of first transitory connector 100 may be disposed in assembled optic fiber fixture 500 wherein superior arm barb 123 is disposed in proximal barb interface 550 and inferior arm barb 133 is disposed in proximal barb interface 550. Illustratively, a portion of first transitory connector 100 may be disposed in assembled optic fiber fixture 500 wherein superior arm barb 123 is in contact with an outer perimeter of proximal barb interface 550 and wherein inferior arm barb 133 is in contact with the outer perimeter of proximal barb interface 550. In one or more embodiments, a portion of first transitory connector 100 may be disposed in assembled optic fiber fixture 500 wherein superior arm 120 and inferior arm 130 are disposed in proximal arm interface 555. Illustratively, a portion of first transitory connector 100 may be disposed in assembled optic fiber fixture 500 wherein superior arm 120 is in contact with an outer perimeter of proximal arm interface 555 and wherein inferior arm 130 is in contact with the outer perimeter of proximal arm interface 555. In one or more embodiments, transitory connector proximal housing proximal taper 545 may be configured to prevent superior arm barb 123 and inferior arm barb 133 from advancing into transitory connector proximal housing 540, e.g., a portion of superior arm barb 123 and a portion of inferior arm barb 133 may contact an outer perimeter of transitory connector proximal housing proximal taper 545.

Illustratively, inserting a portion of first transitory connector 100 into transitory connector proximal housing 540 may be configured to ingress optic fiber proximal end 212 into transitory connector proximal housing distal taper 535. In one or more embodiments, transitory connector proximal housing distal taper 535 may be configured to guide an ingress of optic fiber proximal end 212 into fixture base inner bore 530. Illustratively, fixture base inner bore 530 may be configured to guide an ingress of optic fiber proximal end 212 into machine connector proximal inner lumen 525. In one or more embodiments, inner lumen proximal taper 520 may be configured to guide an ingress of optic fiber proximal end 212 into machine connector distal inner lumen 515. Illustratively, inner lumen distal taper 510 may be configured to guide an ingress of optic fiber proximal end 212 into optic fiber proximal end guide 505. In one or more embodiments, a distance that optic fiber proximal end 212 extends from first transitory connector distal end 101 may be configured to cause optic fiber proximal end 212 to be adjacent to assembled ops tic fiber fixture proximal end 502 when first transitory connector 100 is inserted into transitory connector proximal housing 540.

In one or more embodiments, a portion of a second transitory connector 100 may be disposed in illumination optic fiber fixture 2100, e.g., second transitory connector distal end 101 may be disposed in transitory connector proximal housing 2130. Illustratively, a portion of second transitory connector 100 may extend a distance from illumination optic fiber fixture proximal end 2102, e.g., second transitory connector proximal end 102 may extend a distance from illumination optic fiber fixture proximal end 2102. In one or more embodiments, a portion of second transitory connector 100 may be disposed in illumination optic fiber fixture 2100 wherein superior arm barb 123 is disposed in proxies mal barb interface 2150 and inferior arm barb 133 is disposed in proximal barb interface 2150. Illustratively, a portion of second transitory connector 100 may be disposed in illumination optic fiber fixture 2100 wherein superior arm barb 123 is in contact with an outer perimeter of proximal barb interface 2150 and wherein inferior arm barb 133 is in contact with the outer perimeter of proximal barb interface 2150. In one or more embodiments, a portion of second transitory connector 100 may be disposed in illumination optic fiber fixture 2100 wherein superior arm 120 and inferior arm 130 are disposed in proximal arm interface 2155. Illustratively, a portion of second transitory connector 100 may be disposed in illumination optic fiber fixture 2100 wherein superior arm 120 is in contact with an outer perimeter of proximal arm interface 2155 and wherein inferior arm 130 is in contact with the outer perimeter of proximal arm interface 2155. In one or more embodiments, transitory connector proximal housing proximal taper 2135 may be configured to prevent superior arm barb 123 and inferior arm barb 133 from advancing into transitory connector proximal housing 2130, e.g., a portion of superior arm barb 123 and a portion of inferior arm barb 133 may contact an outer perimeter of transitory connector proximal housing proximal taper 2135.

Illustratively, inserting a portion of second transitory connector 100 into transitory connector proximal housing 2130 may be configured to ingress illumination optic fiber proximal end 1922 into transitory connector proximal housing distal taper 2145. In one or more embodiments, transitory connector proximal housing distal taper 2145 may be configured to guide an ingress of illumination optic fiber proximal end 1922 into illumination optic fiber fixture inner bore 2140. Illustratively, illumination optic fiber fixture inner bore 2140 may be configured to guide an ingress of illumination optic fiber proximal end 1922 into illumination optic fiber fixture inner bore distal taper 2146. In one or more embodiments, illumination optic fiber fixture inner bore distal taper 2146 may be configured to guide an ingress of illumination optic fiber proximal end 1922 into illumination optic fiber guide 2105. Illustratively, a distance that illumination optic fiber proximal end 1922 extends from second transitory connector distal end 101 may be configured to cause illumination optic fiber proximal end 1922 to be adjacent to illumination optic fiber fixture distal end 2101 when second transitory connector 100 is inserted into transitory connector proximal housing 2130.

Illustratively, a user may perform an illuminated photocoagulation procedure with assembled illuminated laser probe with replaceable fibers 2200. In one or more embodiments, a user may connect machine connector 440 to a laser machine. Illustratively, a user may energize the laser machine to deliver laser light into optic fiber proximal end 212, through optic fiber 210, out from optic fiber distal end 211, and onto a surgical target site. In one or more embodiments, a user may connect illumination machine connector

2120 to an illumination machine. Illustratively, a user may energize the illumination machine to deliver illumination light into illuminated optic fiber proximal end 1922, through illuminated optic fiber 1920, out from illumination optic fiber distal end 1921, and onto a surgical target site. In one or more embodiments, illumination optic fiber fixture 2100 may be a reusable medical device sold non-sterile and sterilized by a user in a medical autoclave. Illustratively, assembled illuminated handle 2000 may be a single-use medical device sold sterile and discarded after use. In one or more embodiments, assembled illuminated handle 2000 may be manufactured with an assembled curved hypodermic tube 1100 instead of illumination hypodermic tube 1980. Illustratively, illuminated handle 2000 may be manufactured with an assembled steerable handle 1700 instead of illumination handle base 1970 and illumination hypodermic tube 1980.

In one or more embodiments, optic fiber 210 may from glass, e.g., optic fiber 210 may be manufactured from silica. Illustratively, optic fiber 210 may comprise a plurality of optic fibers 210. In one or more embodiments, illumination optic fiber 1920 may comprise a plurality of illumination optic fibers 1920. Illustratively, illumination optic fiber 1920 may comprise one or more optic fibers manufactured from plastic, e.g., illumination optic fiber 1920 may comprise one or more optic fibers manufactured from Polymethyl Methacrylate Resin, Polystyrene, etc. In one or more embodiments, illumination optic fiber 1920 may comprise one or more optic fibers having a cladding material, e.g., illumination optic fiber 1920 may comprise one or more optic fibers having a cladding material manufactured from a fluorinated polymer, a silicone resin, etc. Illustratively, illumination optic fiber 1920 may comprise one or more optic fibers having a step index refractive index profile. In one or more embodiments, illumination optic fiber 1920 may comprise one or more multi-mode optic fibers, one or more single-mode optic fibers, etc. In one or more embodiments, illumination optic fiber 1920 may comprise one or more optic fibers having a core refractive index in a range of 1.3 to 1.8, e.g., illumination optic fiber 1920 may comprise one or more optic fibers having a core refractive index of 1.49. Illustratively, illumination optic fiber 1920 may comprise one or more optic fibers having a core refractive index of less than 1.3 or greater than 1.8. In one or more embodiments, illumination optic fiber 1920 may comprise one or more optic fibers having a numerical aperture in a range of 0.3 to 0.8, e.g., illumination optic fiber 1920 may comprise one or more optic fibers having a numerical aperture of 0.5. In one or more embodiments, illumination optic fiber 1920 may comprise one or more optic fibers having a numerical aperture of less than 0.3 or greater than 0.8. Illustratively, illumination optic fiber 1920 may comprise one or more optic fibers having a core diameter in a range of 85 to 285 micrometers, e.g., illumination optic fiber 1920 may comprise one or more optic fibers having a core diameter of 135 micrometers. In one or more embodiments, illumination optic fiber 1920 may comprise one or more optic fibers having a core diameter of less than 85 micrometers or greater than 285 micrometers. Illustratively, illumination optic fiber 1920 may comprise one or more optic fibers having an overall diameter in a range of 100 to 300 micrometers, e.g., illumination optic fiber 1920 may comprise one or more optic fiber having an overall diameter of 200 micrometers. In one or more embodiments, illumination optic fiber 1920 may comprise one or more optic fibers having an overall diameter of less than 100 or greater than 300 micrometers.

The foregoing description has been directed to particular embodiments of this invention. It will be apparent; however, that other variations and modifications may be made to the described embodiments, with the attainment of some or all of their advantages. Specifically, it should be noted that the principles of the present invention may be implemented in any system. Furthermore, while this description has been written in terms of a laser probe, the teachings of the present invention are equally suitable to any systems where the functionality may be employed. Therefore, it is the object of the appended claims to cover all such variations and modifications as come within the true spirit and scope of the invention.

What is claimed is:

1. An instrument system comprising:
   a handle assembly having a handle, a hypodermic tube, a wire, a slider, a piston with a slot, and expansion ring disposed in a portion of the piston;
   a first transitory connector having a first transitory connector distal end and a first transitory connector proximal end wherein the first transitory connector is manufactured from a material configured to deform if the first transitory connector is sterilized in a medical autoclave;
   a proximal base of the first transitory connector having a proximal base distal end and a proximal base proximal end wherein the proximal base proximal end is the first transitory connector proximal end;
   a distal base of the first transitory connector wherein the distal base is disposed between the first transitory connector distal end and the proximal base distal end;
   a tapered inner lumen of the first transitory connector;
   a first superior arm of the first transitory connector having a first superior arm distal end and a first superior arm proximal end wherein the first superior arm is disposed between the first transitory connector distal end and the first transitory connector proximal end;
   a first superior arm barb of the first superior arm wherein the first superior arm barb is disposed between the first superior arm distal end and the first superior arm proximal end;
   a first inferior arm of the first transitory connector having a first inferior arm distal end and a first inferior arm proximal end;
   a first inferior arm barb of the first inferior arm wherein the first inferior arm barb is disposed between the first inferior arm distal end and the first inferior arm proximal end;
   a second transitory connector having a second transitory connector distal end and a second transitory connector proximal end;
   a tapered inner lumen of the second transitory connector;
   a second superior arm of the second transitory connector having a second superior arm distal end and a second superior arm proximal end;
   a second superior arm barb of the second superior arm wherein the second superior arm barb is disposed between the second superior arm distal end and the second superior arm proximal end;
   a second inferior arm of the second transitory connector having a second inferior arm distal end and a second inferior arm proximal end;
   a second inferior arm barb of the second inferior arm wherein the second inferior arm barb is disposed between the second inferior arm distal end and the second inferior arm proximal end; and an optic fiber having an optic fiber distal end and an optic fiber proximal end, the optic fiber disposed in the tapered inner lumen of the first transitory connector wherein the optic fiber distal end extends a distance from the first transitory connector distal end.

2. The instrument system of claim 1 wherein the optic fiber is disposed in the tapered inner lumen of the second transitory connector wherein the optic fiber proximal end extends a distance from the second transitory connector distal end.

3. The instrument system of claim 2 wherein the distance that the optic fiber distal end extends from the first transitory connector distal end is equal to the distance that the optic fiber proximal end extends from the second transitory connector distal end.

4. The instrument system of claim 1 further comprising:
a jacketing having a jacketing distal end and a jacketing proximal end, the jacketing disposed over a portion of the optic fiber.

5. The instrument system of claim 1 further comprising:
an illumination optic fiber having an illumination optic fiber distal end and an illumination optic fiber proximal end.

6. The instrument system of claim 5 wherein the illumination optic fiber is disposed in the tapered inner lumen of the second transitory connector wherein the illumination optic fiber proximal end extends a distance from the second transitory connector distal end.

7. The instrument system of claim 6 wherein the distance that the optic fiber distal end extends from the first transitory connector distal end is not equal to the distance that the illumination optic fiber proximal end extends from the second transitory connector distal end.

8. The instrument system of claim 1 further comprising:
an optic fiber fixture having an optic fiber fixture distal end and an optic fiber fixture proximal end.

9. The instrument system of claim 8 further comprising:
a fixture base of the optic fiber fixture having a fixture base distal end and a fixture base proximal end.

10. The instrument system of claim 9 further comprising:
a machine connector housing of the optic fiber fixture having a machine connector housing distal end and a machine connector housing proximal end.

11. The instrument system of claim 10 further comprising:
an extender of the optic fiber fixture having an extender distal end and an extender proximal end.

12. The instrument system of claim 11 further comprising:
a machine connector of the optic fiber fixture having a machine connector distal end and a machine connector proximal end.

13. The instrument system of claim 12 further comprising:
a machine coupler of the optic fiber fixture.

14. The instrument system of claim 12 further comprising:
an electrical element of the optic fiber fixture.

15. The instrument system of claim 12 further comprising:
an illumination optic fiber fixture having an illumination optic fiber fixture distal end and an illumination optic fiber fixture proximal end.

16. The instrument system of claim 1 wherein the first transitory connector is manufactured by injection molding.

* * * * *